US005853765A

United States Patent [19]
Stolle et al.

[11] Patent Number: 5,853,765
[45] Date of Patent: Dec. 29, 1998

[54] ANTI-CHOLESTEROLEMIC EGG, VACCINE AND METHOD FOR PRODUCTION, AND USE

[75] Inventors: Ralph J. Stolle; Lee R. Beck, both of Lebanon, Ohio

[73] Assignee: DCV, Inc., Wilmington, Del.

[21] Appl. No.: 487,419

[22] Filed: Jun. 7, 1995

Related U.S. Application Data

[60] Division of Ser. No. 67,088, May 26, 1993, abandoned, which is a continuation-in-part of Ser. No. 658,437, Feb. 20, 1991, abandoned, which is a continuation of Ser. No. 1,842, Jan. 9, 1987, abandoned, which is a continuation-in-part of Ser. No. 546,162, Oct. 27, 1983, Pat. No. 4,636,384, which is a continuation-in-part of Ser. No. 384,625, Jun. 3, 1982, abandoned, which is a continuation-in-part of Ser. No. 622,130, Jun. 19, 1984, Pat. No. 4,748,018, which is a continuation-in-part of Ser. No. 577,804, Feb. 7, 1984, abandoned.

[51] Int. Cl.$^6$ .......................... A61K 35/54; A61K 39/02; A61K 45/00; A61K 47/00
[52] U.S. Cl. ....................... 424/581; 424/439; 424/234.1; 424/282.1
[58] Field of Search ................................ 426/614, 417, 426/480, 271, 425, 429, 478, 573, 575; 424/157.1, 203.1, 581, 439, 234.1, 282.1; 800/2; 119/6.8

[56] References Cited

U.S. PATENT DOCUMENTS

| | | | |
|---|---|---|---|
| 3,128,230 | 4/1964 | Heinbach | 167/78 |
| 3,376,198 | 4/1968 | Petersen | 167/78 |
| 4,284,623 | 8/1981 | Beck | 424/85 |
| 4,324,782 | 4/1982 | Beck | 424/87 |
| 4,357,272 | 11/1982 | Polson | 260/112 |
| 4,410,541 | 10/1983 | Kamimae et al. | 424/273 R |
| 4,536,384 | 8/1985 | Stolle | 424/87 |
| 4,550,019 | 10/1985 | Polson | 424/85 |
| 4,748,018 | 5/1988 | Stolle et al. | 424/87 |
| 4,764,531 | 8/1988 | Nissen | 514/557 |
| 4,812,441 | 3/1989 | Kawai | 514/2 |
| 4,897,265 | 1/1990 | Stolle | 424/87 |
| 4,956,349 | 9/1990 | Beck | 514/54 |
| 5,215,746 | 6/1993 | Stolle et al. | 424/92 |

FOREIGN PATENT DOCUMENTS

| | | |
|---|---|---|
| 0 143 345 | 6/1985 | European Pat. Off. . |
| 0 152 270 | 8/1985 | European Pat. Off. . |
| 2397839 | 7/1977 | France . |
| 1211876 | 11/1970 | United Kingdom . |
| 1442283 | 7/1976 | United Kingdom . |

OTHER PUBLICATIONS

Ali, Genetic parameters associated with cholesterol in egg yolk and blood serum of the chicken, *Dissertation Abstracts, Int. B.* 28(4):1548 (1977).

Arp, Consequences of active or passive immunization of turkeys against *Escherichia coli* 078, *Avian Diseases* 24:808–815 (1980).

Bierman, Atherosclerosis and other forms of arteriosclerosis, in Harrison, *Principles of Internal Medicine*, 10th ed., pp. 1465–1475 (1983), McGraw–Hill Publishers, N.Y.

Burley et al., Chromatographic separation of the soluble proteins of hen's egg yolk: an analytical and preparative study, *Anal. Biochem.* 94:53–59 (1979).

Duff et al., The effect of alloxan diabetes on experimental cholesterol atherosclerosis in the rabbit, *J. Exp. Med.* 89:611–630 (1949).

Fertel et al., Formation of antibodies to prostaglandins in the yolk of chicken eggs, *Biochem. Biophys. Res. Comm.* 102:1028–1033 (1981).

Guyton et al., Early extracellular and cellular lipid deposits in aorta of cholesterol–fed rabbits, *Am. J. Pathol.* 141:925–936 (1992).

Hajjar et al., Signal transduction in atherosclerosis: integration of cytokines and the eicosanoid network, *The FASEB Journal* 6:2933–2941 (1992).

Jensenius et al., Eggs: conveniently packaged antibodies. Methods for purification of yolk IgG, *J. Immunol. Methods* 46:63–68 (1981).

Lebacq–Verheyden et al., Qualification and distribution of chicken immunoglobulins IgA, IgM and IgG in serum and secretions, *Immunol.* 27:683–691 (1974).

Leslie et al., Phylogeny of immunoglobulin structure and function, *J. Exp. Med.* 130:1337–1352 (1969).

Markley et al., Protection by vaccination against Pseudomonas infection after thermal injury, *J. Bacteriol.* 96:867–874 (1968).

Martin et al., Preparation and molecular weight of γ–livetin from egg yolk, *Can. J. Biochem. Physiol.* 36:153–160 (1958).

*Microbiology*, (Davis et al., eds.), 3rd ed., Harper & Row Publishers, p. 294 (1980).

*Microbiology*, (Davis et al., eds.), 3rd ed., Harper & Row Publishers, pp. 656–665 (1980).

(List continued on next page.)

*Primary Examiner*—Jasemine C. Chambers
*Assistant Examiner*—Deborah J. R. Clark
*Attorney, Agent, or Firm*—Bell Seltzer Intellectual Property Law Group of Alston & Bird LLP

[57] ABSTRACT

The present invention is directed to the treatment of vascular disorders particularly arteriosclerosis and atherosclerosis in warm-blooded animals. The invention encompasses the ingestion, by warm-blooded animals, of eggs or egg fractions derived from female avians that have been hyperimmunized with specific bacterial antigens or groups of bacterial antigens. The invention is directed to methods of controlling cholesterol levels, lipid deposits, and the development of atheromatous lesions in warm-blooded animals by the ingestion of eggs or fractions thereof produced in female avians hyperimmunized with specific bacterial antigens. The invention is also directed to methods of producing the eggs and to vaccines for hyperimmunization of the female avians.

18 Claims, 5 Drawing Sheets

OTHER PUBLICATIONS

Padmanaban et al., Cross–protection against fowl typhoid ii. hypersensitivity reactions and quantitative estimation of the elimination of the challenge organisms, *Dev. & Comp. Immunol.* 5:475–481 (1981).

Polson et al., Antibodies to proteins from yolk of immunized hens, *Immunol. Comm.* 9:495–514 (1980).

Raettig, An oral and enteritis–vaccine composed of twelve heat inactivated Enterobacteriaceae. 1. Communication: Theoretical and epidemiological considerations, *Zentralbl. Bakteriol.* 245:287–300 (1979). (English abstract only).

Siegel et al., Agglutinin responses to *Salmonella pullorum* in Japanese quail selected for plasma cholesterol response to adrenocorticotropin and a model describing the dynamics of the response, *Poultry Science* 63:1892–1894 (1984).

Vesselinovitch et el., Comparison of primates and rabbits as animal models is experimental atherosclerosis, *Advances in Exp. Med. & Biol.* 82:614–619 (1978).

Sugano, O. et al., Manufacture of tocopherol–high eggs, Abstract of Jpn. Kokai Tokkyo Koho JP 62 56, 431, published Mar. 12, 1987, *Chemical Abstracts 107*:628, Abstract No. 174969r (1987).

Owens, J. J. The egg yolk reaction produced by several species of bacteria. J. appl. Bact. vol. 37, pp. 137–148, 1974.

NIH Panel. Report and recommendations of the panel to assess the NIH investment in research on gene therapy, Dec. 7, 1995.

| mg % CHOLESTEROL | | % AORTA WITH SUDANOPHILIC PLAQUE | | SEVERITY OF AORTIC LESIONS | | SEVERITY OF CORONARY LESIONS | |
|---|---|---|---|---|---|---|---|
| 632 | -5 | 68 | -5 | 3.82 | -5 | 2.50 | -2,5 |
| 501 | -2 | 57 | -1 | 2.82 | -1,3 | | |
| 486 | -1 | 48 | -4,6 | 2.78 | -4 | 1.60 | -6 |
| 474 | -3 | 42 | -3 | | | 1.20 | -4 |
| 410 | -6 | | | 2.50 | -2 | 0.88 | -1 |
| 364 | -4 | 36 | -2 | 2.44 | -6 | 0.70 | -3 |

RANKING FOR GROUPS 1 THROUGH 6

HIGHEST ... LOWEST

FIG. 5

# ANTI-CHOLESTEROLEMIC EGG, VACCINE AND METHOD FOR PRODUCTION, AND USE

CROSS-REFERENCES TO RELATED DOCUMENTS

This application is a division of application Ser. No. 08/067,088, filed May 26, 1993 abandoned; which is a continuation-in-part of application Ser. No. 07/658,437, filed Feb. 20, 1991 abandoned; which is a continuation of application Ser. No. 07/001,842, filed Jan. 9, 1987 abandoned; which is a continuation-in-part of application Ser. No. 06/546,162, filed Oct. 27, 1983 now U.S. Pat. No. 4,636,384 which is a continuation-in-part of application Ser. No. 06/384,625, filed Jun. 3, 1982 abandoned which is a continuation-in-part of application Ser. No. 06/622,130, filed Jun. 19, 1984 now U.S. Pat. No. 4,748,018 which is a continuation-in-part of application Ser. No. 06/577,804, filed Feb. 7, 1984 abandoned.

BACKGROUND OF THE INVENTION

1. Field of the Invention

The present invention relates to avian eggs, egg products, and egg fractions, methods for making the eggs, vaccines, and methods of using the eggs and egg products and fractions. The eggs and egg products contain factors effective for controlling cholesterol in serum and lipids in warm-blooded animals.

The factors are found in eggs and egg products and fractions obtained from animals that have been hyperimmunized. The factors have beneficial effects on the vascular system by lowering or maintaining the levels of serum cholesterol and lipid deposits in animals consuming the eggs or egg products or not elevating the levels of serum cholesterol and lipid deposits to those levels found in animals ingesting untreated eggs. The invention relates to the use of eggs, egg products, and egg fractions for the treatment of disorders of the vascular systems, such as vascular aging and arteriosclerosis. The beneficial effects are produced from ingestion of eggs, egg fractions, or egg products from animals hyperimmunized with specific bacterial antigens.

2. Description of the Background Art

VASCULAR DISORDERS

The normal vascular system of mammals, especially humans, includes all of the organs, such as the heart and the arteries, involved in blood transport and circulation. Two major disorders affect the vascular system in animals: arteriosclerosis and aging. Arteriosclerosis, a generic term for the thickening and hardening of the arterial wall, is responsible for the majority of deaths in the United States and most westernized societies. There are various types of arteriosclerosis, such as atherosclerosis, focal calcification, and arteriosclerosis. The changes associated with arteriosclerosis (of the various types) and aging are partly overlapping. (See, for example, Harrison's "Principles of Internal Medicine," 10th edition, pp. 1465–1475.)

The normal artery wall consists of three reasonably well-defined layers: the intima, the media, and the adventitia. The intima is a layer of endothelial cells lining the lumen of all arteries. The endothelial cells are attached to each other by a series of junctional complexes and also are attached to an underlying meshwork of loose connecting tissue, the basal lamina. The lining of endothelial cells forms a barrier that controls the entry of substances from the blood into the arterial wall. The media consists of smooth muscle cells arranged in either single layers or multiple layers. The outermost layer of the artery is the adventitia which is delimited by the external elastic lamina. This external coat consists of a loose interwoven mixture of thick bundles of collagen, elastic fibers of varying size, and a mixture of smooth muscle cells and fibroblasts.

Maintenance of the endothelial cell lining is critical. Endothelial cell turnover occurs at a slow rate but may accelerate in focal areas by changing patterns of flow along the vessel wall. Intact endothelial cells function to prevent clotting, partly by elaboration of prostacyclin that inhibits platelet function, thereby enhancing unimpeded flow of blood. When the lining is damaged, however, platelets adhere to it, in part as the result of production of a different class of prostaglandins, the thromboxanes, and form a clot. The ability of the arterial wall to maintain the integrity of its endothelium, prevent platelet aggregation, and ensure the nutrition of its middle portion may be the critical determinants of the arteriosclerotic process.

The major change that occurs with normal aging in the arterial wall is a slow symmetrical increase in the thickness of the intima. This results from an accumulation of small muscle cells. In the non-diseased artery wall, the lipid content, mainly cholesterol ester and phospholipid, also progressively increases with age. While most of the phospholipid in the normal artery wall appears to be derived from in situ synthesis, the cholesterol ester that accumulates with aging appears to be derived from plasma, as it contains principally linoleic acid, the major plasma cholesterol ester fatty acid. As the normal artery ages, smooth muscle cells and connective tissue accumulate in the intima, leading to progressive thickening of the layer, coupled with progressive accumulation of fatty acid, resulting in a gradual increase in the rigidity of the vessels. The larger arteries may become dilated, elongated, and porous, and aneurysms may form in areas of encroaching degenerating arteriosclerotic plaque.

By far, the leading cause of death in the United States above age 65, is atherosclerosis, the atheromatous form of arteriosclerosis. Atherosclerosis can be defined in broad terms as a vascular disease accompanied by dysregulation of cholesterol metabolism. This disease and its complications are the principal cause of mortality in the United States.

Progress has been made recently in understanding the basic biology of atherosclerosis (see, e.g., Hajjar, D. P. et al., *FASEB Journal* 6:2933–2941 (1992); Guyton, J. R. et al., *American Journal of Pathology* 141:925–936 (1992)). Yet, these basic data require clinical application if progress is to be made toward treating and preventing this disease.

The lesions are commonly classified as fatty streaks, fibrous plaques, and complicated lesions. The fatty streaks are characterized by an accumulation of lipid-filled smooth muscle cells and fibrous tissue in focal areas of the intima, and are stained distinctively by fat-soluble dyes. The lipid is mainly cholesterol oleate. Fibrous plaques are elevated areas of intima thickening, and will present the most characteristic lesion of advancing arteriosclerosis. They appear in the abdominal aorta, coronary arteries, and carotid arteries in the third decade, and increase progressively with age. Complicated lesions are calcified fibrous plaques containing various degrees of necrosis, thrombosis, and ulceration.

A number of "risk factors" have been identified in individuals who develop atherosclerosis. The risk factor concept implies that a person with at least one risk factor is more likely to develop a clinical atherosclerotic event and to do so earlier than a person with no risk factors. The presence of multiple risk factors further accelerates atherosclerosis. Among the reversible or partially reversible risk factors are hyperlipidemia (hypercholesterolemia and/or hypertriglyceridemia), hyperglycemia and diabetes mellitus, low levels of high-density lipoproteins in the presence of high concentrations of low-density lipoproteins, hypertension, obesity, and cigarette smoking.

As stated in Harrison's, supra (p. 1470), although the emergence of clinical consequences of atherosclerosis can be lessened, no convincing instance of regression or interruption of regression of atherosclerosis by removal or reversal of any single or group of risk factors has yet been proved in humans. The trend toward reduced smoking, lower cholesterol and fat consumption, reduction of body weight, and exercise programs have been helpful. Prevention, rather than treatment, however, is the goal of public health professionals. An effective program of prophylaxis has not yet been established, although enough is known to guide in both identification of high risk and development of measures to reduce the risk.

Among the risk factors referred to above that might be particularly well-suited to therapeutic treatment is hyperlipidemia. Although control of factors such as obesity and cigarette consumption depend, to a great degree, on the will and inclination of individual, if a reasonable method for lowering total serum cholesterol, low-density lipoprotein cholesterol and triglycerides in the circulation were provided, it would be suitable for treatment of a broad spectrum of individuals.

Because of the widespread distribution of vascular disorders such as arteriosclerotic disorders and the naturally occurring aging of the vascular system and its accompanying problems, a need exists for an effective method both for preventing and possibly treating these disorders. If a natural food product, such as milk or eggs, for example, could be obtained having anti-arteriosclerotic and anti-aging effects, it would be an easily administratible, readily available, safe therapeutic composition.

PRODUCTS FROM HYPERIMMUNIZED ANIMALS

It has been known in the prior art to produce milks having a variety of therapeutic effects. Beck, for example, has disclosed a milk containing antibody to *Streptococcus mutans* which has dental caries-inhibiting effects (Beck, U.S. Pat. No. 4,324,782). The milk is obtained by immunizing a cow with *S. mutans* antigen in two stages, and obtaining the therapeutic milk. Beck has also described milk having anti-inflammatory properties (U.S. Pat. No. 4,284,623) and anti-hypertensive properties (U.S. Pat. No. 4,879,110). Heinbach, U.S. Pat. No. 3,128,230, has described milk containing globulins of alpha, beta, and gamma components by inoculating a cow with antigenic mixtures. Petersen (U.S. Pat. No. 3,376,198 Canadian Patent 587,849) and Tunnah et al. (British Patent, 1,211,876) have also described antibody-containing milks.

U.S. Pat. No. 4,897,265 and U.S. Pat. No. 4,636,384 (Reissue No. 33,403) disclose a method for lowering blood lipid concentrations and thereby treating the aforementioned vascular disorders comprising feeding test animals and humans antibody-containing milk derived from cows maintained in a hyperimmune state by injections of polyvalent antigens derived from mixtures of bacteria.

It is known that various genera of the class Aves, such as chickens (*Gallus domesticus*), turkeys, and ducks, produce antibodies in their blood and in their eggs against factors which cause avian diseases, as well as against other antigens. For example, LeBacq-Verheyden et al., *Immunology* 27:683 (1974), and Leslie, G. A., et al., *J. Med.* 130:1337 (1969), have quantitatively analyzed inmunoglobulins of the chicken. Polson, A., et al., *Immunological Communications* 9:495–514 (1980) immunized hens against several proteins and natural mixtures of proteins, and detected IgY antibodies in the yolks of the eggs. Fertel, R., et al., *Biochemical and Biophysical Research Communications* 102:1028–1033 (1981) immunized hens against prostaglandins and detected antibodies in the egg yolk. Jensenius et al., *Journal of Immunological Methods* 46:63–68 (1981), provide a method of isolating egg yolk IgG for use in immunodiagnostics. Polson et al., *Immunological Communications* 9:475–493 (1980), describe antibodies isolated from the yolk of hens that were immunized with a variety of plant viruses.

Polson, U.S. Pat. No. 4,357,272, discloses the isolation of antibodies from the yolks of eggs derived from hyperimmunized hens. The hyperimmunization was elicited by repetitive injections into the hens of antigens represented by plant viruses, human IgG, tetanus antitoxin, snake antivenins, and Serameba antigens. Polson, U.S. Pat. No. 4,550,019, discloses the isolation from egg yolks of antibodies raised in the hen by hyperimmunization with immunogens having a molecular or particle weight of at least 30,000. The antigens used to hyperimmunize the chickens were selected from among plant viruses, human immunoglobulins, tetanus toxin, and snake venoms.

The present invention is a further development over the invention disclosed and claimed in U.S. application Ser. No. 577,804, filed Feb. 4, 1984, by Beck and Stolle, for "Heterologous Protein Antibody Formulation for Passive Immunization," now abandoned, and in U.S. Pat. No. 4,748,018, filed Jun. 19, 1984, by Stolle and Beck, for "Method of Passive Immunization of Mammals Using Avian Antibody." The entire disclosure of said patent is herein incorporated by reference.

In Ser. No. 577,804, there is disclosed a method of passive immunization of a mammal which comprises parenterally injecting a purified heterologous antibody obtained from the eggs of a domesticated fowl, which species has been immunized against an antigenic substance, and wherein the mammal has a history of consumption of eggs from such domesticated fowl. The invention disclosed in U.S. Pat. No. 4,748,018 expands on the concepts disclosed in U.S. Ser. No. 577,804, in that administration of the egg antibody can be by any appropriate route, not only parenteral.

All of these references, however, relate only to immunoglobulins raised against various antigens by hyperimmunization and to the subsequent use of said immunoglobulins for either diagnostic procedures or homologous or heterologous passive immunization. No suggestion or speculation is made in these references either that the milk or eggs from hyperimmunized animals would have a beneficial effect on the vascular system by controlling serum cholesterol concentrations or lipid deposits in animals or that said hyperimmunized eggs could be consumed by humans and other animals without elevating serum lipid concentrations or not elevating them to the levels found in animals consuming normal eggs.

SUMMARY OF THE INVENTION

The invention is based on the inventors' discovery that eggs and egg products obtained from hyperimmunized chickens, when fed to a warm-blooded animal, provide a method for the control of lipid deposits and cholesterol levels in the animal.

The present invention is based on the discovery that the ingestion of eggs or fractions from avians hyperimmunized against specific bacterial strains could achieve the following results:

1. lower the levels of lipid deposits in the aorta compared to levels found in animals not ingesting any eggs;
2. not increase the levels of lipid deposits in tie aorta or liver above the levels found in animals not ingesting eggs;
3. not elevate the levels of lipid deposits in aorta or liver to those levels found in animals ingesting equivalent amounts of untreated eggs;
4. not elevate the levels of serum cholesterol to those levels found in animals ingesting equivalent amounts of untreated eggs.

The present invention is also based on the inventors' discovery that serum cholesterol can be lowered in warm-blooded animals consuming a high-cholesterol diet by the ingestion of eggs or egg fractions from hyperimmunized avians. The fractions include egg yolk, egg yolk protein, primarily IgY, and egg white.

The present invention is further based on the discovery that the development and degree of severity of atheromatous lesions in the aorta and coronary arteries of warm-blooded animals ingesting a high-cholesterol diet, including eggs, could be controlled beneficially by the consumption of eggs or egg fractions produced in hyperimmunized avians. The fractions include egg yolks, egg yolk protein, primarily IgY, and egg white.

The present invention is also based on the discovery that the anti-lipid, anti-cholesterol, anti-arteriosclerotic effects described above could be obtained with eggs produced from chickens hyperimmunized with specific bacterial antigens or specific groups of bacterial antigens.

Accordingly, it is an object of the invention to produce avian eggs, egg products, and egg fractions which, when consumed by humans and other warm-blooded animals, will lower cholesterol and lipids in warm-blooded animals ingesting these eggs or egg fractions.

It is a further object of the invention to provide avian eggs or egg fractions which, when consumed by humans and other warm-blooded animals, will not increase the levels of cholesterol or lipids in animals ingesting these eggs or egg fractions.

It is also an object of the invention to provide avian eggs or egg fractions which will not increase the levels of cholesterol or lipids to those levels found in animals consuming equivalent amounts of normal eggs.

It is a further object of the invention to provide avian eggs and egg fractions having beneficial effects upon disorders of the vascular system, especially atherosclerosis and the development of atheromatous lesions.

Accordingly, a further object of the invention is to provide a method for treating vascular disorders in humans and other warm blooded animals by controlling cholesterol and lipid deposits, such that disease symptoms, such as atheromatous lesions, are prevented or ameliorated.

It is a further object of the invention to control cholesterol levels and the development of arteriosclerosis in animals on a high-cholesterol diet.

Accordingly, the invention generally provides methods for preventing or treating vascular disorders in humans and other warm blooded animals which comprises administering eggs, egg products, or egg fractions derived from avians maintained in a hyperimmune state in an amount sufficient to produce anti-arteriosclerotic, and particularly anti-atherosclerotic effects.

The invention specifically provides a method for preventing or treating vascular disorders in humans and other warm-blooded animals by controlling the levels of cholesterol, and especially serum cholesterol, and lipid deposits in the organs and tissues of said animals by the administration of eggs, egg fractions, or egg products from hyperimmunized avians.

The invention specifically provides avian eggs, fractions, and egg products which, when consumed by a warm-blooded animal, lowers cholesterol or lipid deposits in that animal.

The present invention also specifically provides avian eggs, fractions, and egg products which, when consumed by an animal, do not elevate the levels of lipid deposits in the animal.

The present invention further specifically provides avian eggs, fractions, and egg products which, when consumed by an animal, do not elevate the levels of lipids and serum cholesterol to those levels found in animals ingesting equivalent amounts of normal untreated eggs.

The invention also specifically provides avian eggs, fractions, and egg products which, when consumed by a warm-blooded animal on a high-cholesterol diet, significantly lowers the serum cholesterol levels in the animals.

The invention also specifically provides avian eggs, fractions, and egg products which, when consumed by a warm-blooded animal ingesting a high-cholesterol diet and further ingesting normal untreated eggs, significantly lowers serum cholesterol levels from those levels found in animals consuming a high-cholesterol diet and equivalent amounts of normal untreated eggs.

The invention also specifically provides avian eggs, fractions, and egg products which, upon consumption by an animal on a high-holesterol diet and further consuming untreated eggs, markedly reduces the percentage of atheromatous lesions in the animal compared to the percent found in animals on a high-cholesterol diet and consuming equivalent amounts of normal untreated eggs.

The invention further provides avian eggs, fractions, and egg products which, upon consumption by a warm-blooded animal, reduces the degree of severity of atheromatous lesions developed in an animal on a high-cholesterol diet and also consuming normal untreated eggs.

The invention further specifically provides avian eggs, fractions, and egg products which, upon consumption by a warm-blooded animal, on a normal diet or on a high-cholesterol diet, reduce the degree of severity of atheromatous lesions developed in the coronary arteries of these animals.

The present invention also provides methods of producing the eggs or egg products having the beneficial results summarized above. The methods encompass the hyperimmunization of female avians with specific bacterial antigens and subgroups of antigens.

Accordingly, the present invention also provides vaccines comprising bacterial antigens and subgroups of bacterial antigens which, when used to hyperimmunize female egg-laying avians, provide the objects of the present invention.

The present invention also provides various fractions produced from eggs that are derived from hyperimmunized avians and which provide the objects of the present invention when ingested by a warm-blooded animal. The fractions include the egg white, egg yolk, and a purified immunoglobulin-containing fraction from the egg yolk.

Group Number

1N=5 High Cholesterol Diet plus Immune Egg Yolk, 12 weeks.

2N=5 High Cholesterol Diet plus Water, 12 weeks.

3N=5 High Cholesterol Diet plus Immune Whole Eggs, 12 weeks.

4N=5 High Cholesterol Diet plus Immune Egg Yolk Protein (IgY), 12 weeks.

5N=5 High Cholesterol Diet plus Control Whole Eggs, 12 weeks.

6N=5 High Cholesterol Diet plus Immune Egg White, 12 weeks,

7N=5 Standard Diet plus Water, 12 weeks.

Numeral above bar is mean for group.

Figure 2:
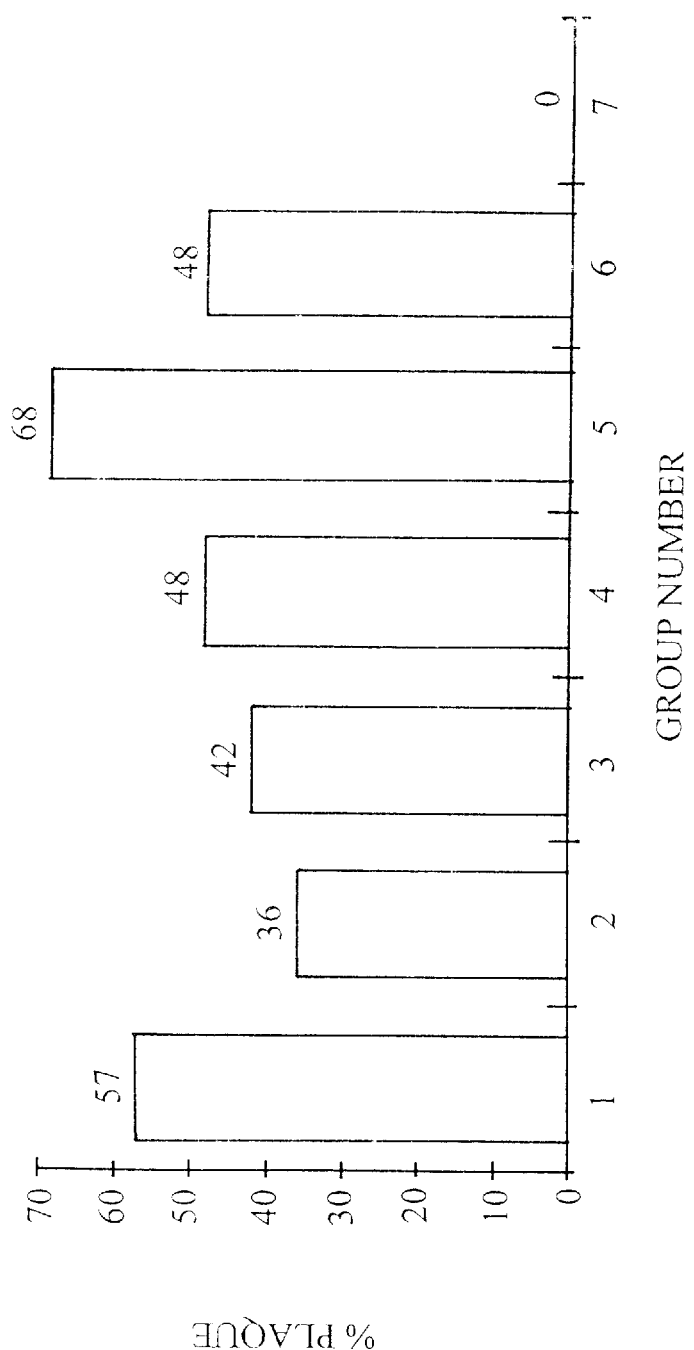

FIG. 2 shows the percentage of plaque (sudanophilic atheromatous lesions) summarized for each group of rabbits. The horizontal axis shows the group number. The vertical axis shows the percent plaque. An explanation of the group numbers is found in the text underneath the figure. The dietary regimen is described in Example 2.

Group Number

1N=5 High Cholesterol Diet plus Immune Egg Yolk, 12 weeks.

2N=5 High Cholesterol Diet plus Water, 12 weeks.

3N=5 High Cholesterol Diet plus Immune Whole Eggs, 12 weeks.

4N=5 High Cholesterol Diet plus Immune Egg Yolk Protein (IgY), 12 weeks.

5N=5 High Cholesterol Diet plus Control Whole Eggs, 12 weeks.

6N=5 High Cholesterol Diet plus Immune Egg White, 12 weeks.

7N=5 Standard Diet plus Water, 12 weeks.

Numeral above bar is mean for group. Percent plaque was measured by automated image analysis.

Figure 3:
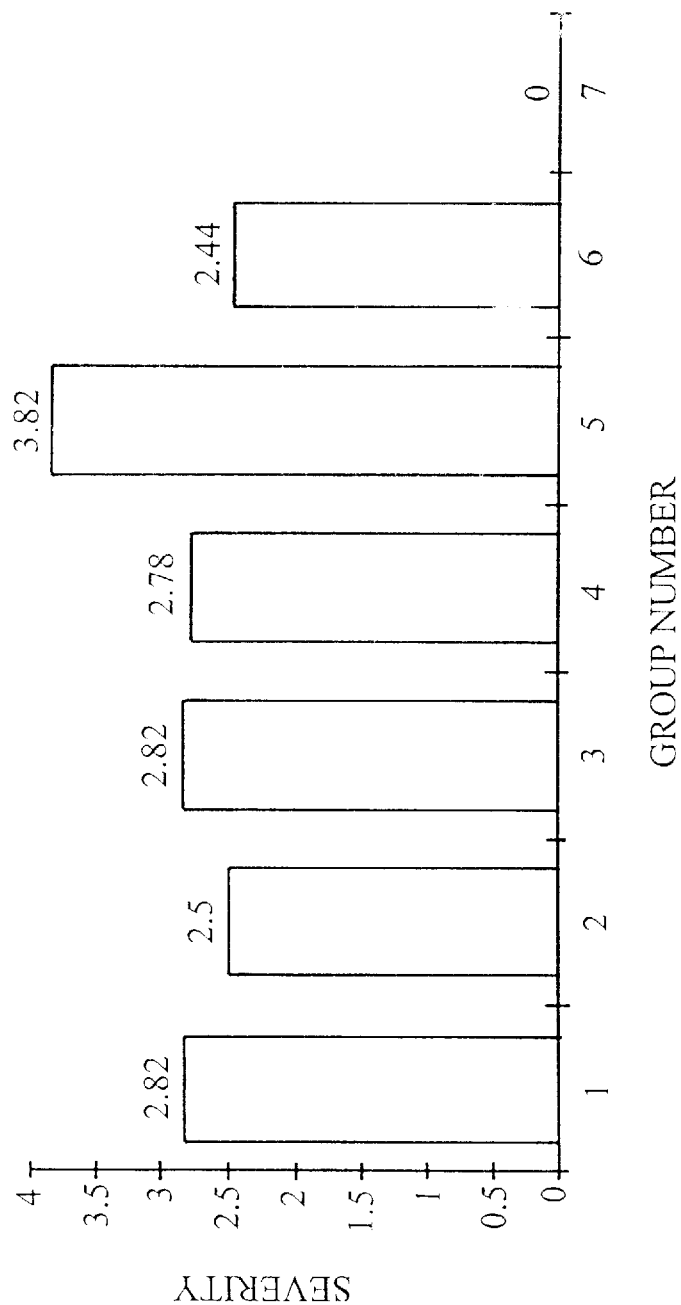

FIG. 3 summarizes the degree of severity of atheromatous lesions in the aortas of each group of rabbits. The horizontal axis shows the group number. The vertical axis shows the severity of lesions. An explanation of the group numbers is found in the text underneath the figure. The dietary regimens are described in Example 2.

Group Number

1N=5 High Cholesterol Diet plus Immune Egg Yolk, 12 weeks.

2N=5 High Cholesterol Diet plus Water, 12 weeks.

3N=5 High Cholesterol Diet plus Immune Whole Eggs, 12 weeks.

4N=5 High Cholesterol Diet plus Immune Egg Yolk Protein (IgY), 12 weeks.

5N=5 High Cholesterol Diet plus Control Whole Eggs, 12 weeks.

6N=5 High Cholesterol Diet plus Immune Egg White, 12 weeks.

7N=5 Standard Diet plus Water, 12 weeks.

Numeral above bar is mean for group. Lesions were determined microscopically in histological sections of aortas.

Figure 4:
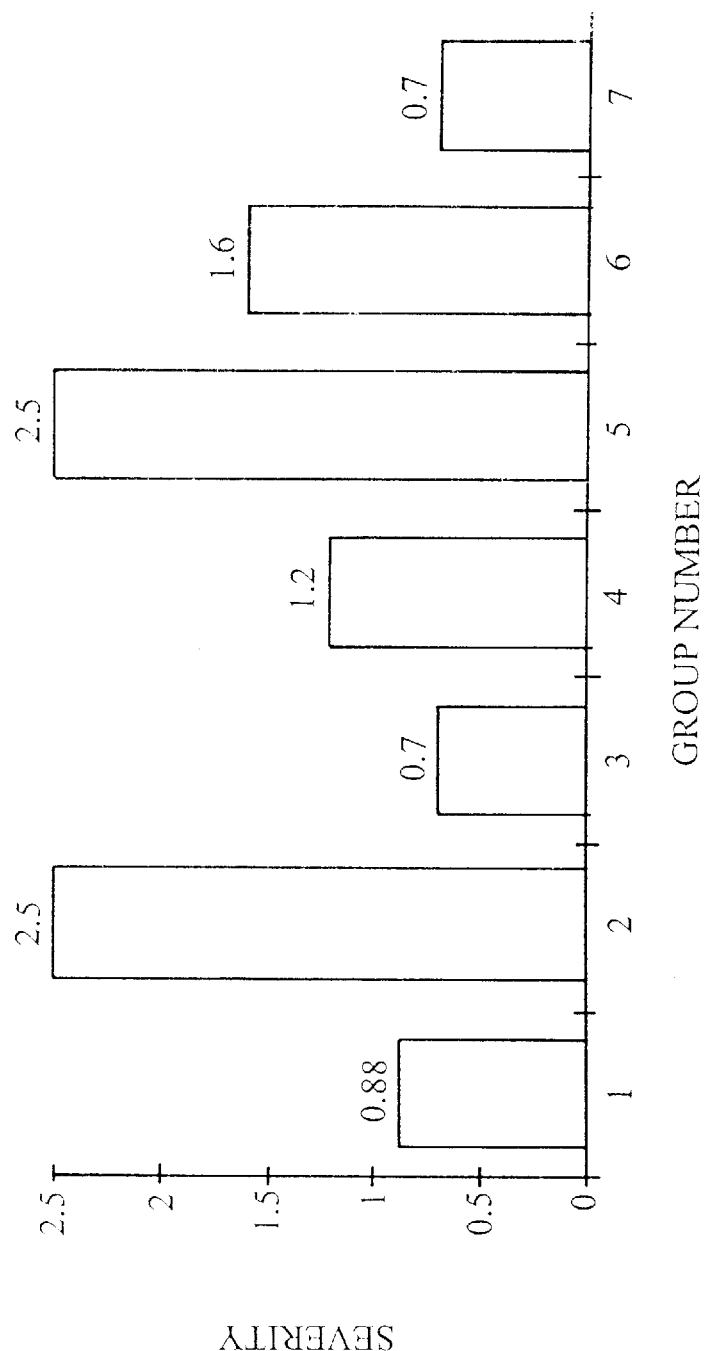

FIG. 4 shows a summary of the degree of severity of atheromatous lesions in the coronary arteries of each group of rabbits. The horizontal axis shows the group number. The vertical axis shows the severity of the lesions. An explanation of the group numbers is found in the text underneath the figure. The dietary regimen is explained in Example 2.

Group Number

1N=5 High Cholesterol Diet plus Immune Egg Yolk, 12 weeks.

2N=5 High Cholesterol Diet plus Water, 12 weeks.

3N=5 High Cholesterol Diet plus Immune Whole Eggs, 12 weeks.

4N=5 High Cholesterol Diet plus Immune Egg Yolk Protein (IgY), 12 weeks.

5N=5 High Cholesterol Diet plus Control Whole Eggs, 12 weeks.

6N=5 High Cholesterol Diet plus Immune Egg White, 12 weeks.

7N=5 Standard Diet plus Water, 12 weeks.

Numeral above bar is mean for group. Lesions were determined microscopically in histological sections of coronary arteries.

FIG. 5 shows a summary of ranks from the highest to the lowest for groups of rabbits on a high-cholesterol diet and receiving control whole eggs, immune whole eggs, or a component of immune eggs (yolks, whites, or IgY). The dietary regimen and other experimental data generating the figure are explained in Example 2. FIG. 5 basically summarizes the result shown in FIGS. 1–4.

Group Number

1N=5 High Cholesterol Diet plus Immune Egg Yolk, 12 weeks.

2N=5 High Cholesterol Diet plus Water, 12 weeks.

3N=5 High Cholesterol Diet plus Immune Whole Eggs, 12 weeks.

4N=5 High Cholesterol Diet plus Immune Egg Yolk Protein (IgY), 12 weeks.

5N=5 High Cholesterol Diet plus Control Whole Eggs, 12 weeks.

6N=5 High Cholesterol Diet plus Immune Egg White, 12 weeks.

DETAILED DESCRIPTION OF THE PREFERRED EMBODIMENTS

The present invention is based on the inventors' discovery that natural food products have beneficial effects on the mammalian vascular system. The eggs and egg products of the present invention, being natural products, can be used to treat vascular disorders associated with arteriosclerotic disease in animals and humans without the fear of toxic side effects.

The present invention is based on the inventors' unexpected discovery that the ingestion of eggs from hyperimmunized chickens has profound effects upon the levels of serum cholesterol and lipid deposits in warm-blooded animals ingesting the eggs. Specifically, autopsy scores of rabbits showed that lipid deposits in the aorta were lowered by the ingestion of the eggs from hyperimmunized chickens, lipid deposits in the aorta and liver were not increased by the ingestion of eggs from hyperimmunized chickens, and lipids in the aorta and liver and levels of cholesterol in the serum were not elevated to those levels found in rabbits ingesting equivalent amounts of normal eggs.

The present invention is also based on the discovery that eggs obtained from chickens hyperimmunized with specific bacterial antigens produced the effects on cholesterol and lipids described above.

The present invention is also based on the discovery that eggs or specific fractions of eggs from hyperimmunized chickens, when ingested by warm-blooded animals on a high-cholesterol diet, provide the following effects on serum cholesterol in these animals: (1) lower the serum cholesterol levels compared to those levels found in an animal on a high-cholesterol diet but not ingesting any eggs; (2) do not-elevate the serum cholesterol to the level found in the animal ingesting equivalent amounts of untreated normal eggs.

The present invention is also based on the discovery that the development of atheromatous lesions (plaque) in animals fed a high-cholesterol diet and also fed eggs or egg fractions from hyperimmunized animals was markedly lower than the development of atheromatous lesions found in warm-blooded animals ingesting a high-cholesterol diet and further ingesting equivalent amounts of untreated eggs.

The present invention is also based on the discovery that the degree of severity of atheromatous lesions in the aorta of animals fed a high-cholesterol diet and also fed eggs or egg fractions from hyperimmunized animals was essentially equivalent to or markedly lower than the degree of severity of lesions in the aortas of warm-blooded animals ingesting a high-cholesterol diet without the ingestion of normal eggs and markedly lower than the degree of severity of lesions in the aortas of animals ingesting a high-cholesterol diet with the further ingestion of equivalents amounts of normal untreated eggs.

The present invention is also based on the discovery that the degree of severity of atheromatous lesions in the coronary arteries of animals fed a high-cholesterol diet and also fed eggs or egg fractions from hyperimmunized animals was equivalent to the degree of severity in animals on a standard diet (non-high-cholesterol) or was markedly lower than the degree of severity of lesions in the coronary arteries of animals ingesting a high-cholesterol diet with or without the further ingestion of normal untreated eggs.

The present invention is also based on the discovery that the effects described above are obtained by hyperimmunizing chickens with specific bacterial antigens.

The present invention is also based on the discovery that the beneficial effects described above could be obtained from whole eggs obtained from hyperimmunized chickens, egg yolks derived from eggs of hyperimmunized chickens, egg yolk protein (IgY fraction) from eggs of hyperimmunized chickens, or egg white (albumin) fraction of eggs from hyperimmunized chickens.

Accordingly, in broad embodiments of the invention, a method is provided for preventing or treating arteriosclerosis, and particularly atherosclerosis, by controlling serum cholesterol and lipid deposits in warm-blooded animals by administering to said animal eggs or egg fractions derived from female avians hyperimmunized with various bacterial antigens.

Accordingly, in one embodiment, a method is provided for reducing lipid deposits and serum cholesterol levels in animals comprising the administration of egg or egg fractions derived from the eggs of female avians that have been hyperimmunized with specific bacterial antigens.

In a further embodiment, a method is provided for reducing the development of plaque (atheromatous lesions) in animals comprising the administration of egg and egg fractions derived from eggs from female avians that have been hyperimmunized with specific bacterial antigens.

In specific embodiments, the effects are achieved in the coronary arteries and/or aortas of the animals.

In a further embodiment, a method is provided for controlling the degree of the severity of atheromatous lesions in animals comprising the administration of egg or egg fraction derived from eggs produced in female avians that have been hyperimmunized with specific bacterial antigens.

In a specific embodiment, a method is provided for controlling the degree of severity in atheromatous lesions in the aortas of warm-blooded animals comprising administering egg or egg fraction derived from eggs produced in female avians hyperimmunized with specific bacterial antigens.

In a further specific embodiment of the invention, a method of controlling the degree of severity of atheromatous lesions in coronary arteries of warm-blooded animals is provided comprising the administration of egg or egg fraction derived from female avians hyperimmunized with specific bacterial antigens.

In other specific embodiments, the above effects are achieved with animals on a high cholesterol diet. The animal on a high cholesterol diet may also be consuming normal untreated eggs or egg products.

In preferred specific embodiments of the present invention, a method is provided for controlling serum cholesterol levels in a warm-blooded animal by the administration of egg yolks, whole eggs, egg yolk protein (IgY fraction), or egg white from eggs derived from female avians that have been hyperimmunized with the Stolle S-100 series vaccine.

In further preferred specific embodiments of the invention, a method is provided for reducing the development of atheromatous lesions (plaques) in warm-blooded animals comprising the administration of egg yolks, whole eggs, egg yolk protein (IgY fraction), or egg white from eggs derived from female avians that have been hyperimmunized with the Stolle S-100 series vaccine.

In further specific preferred embodiments of the invention a method is provided for controlling the degree of severity of atheromatous lesions in warm-blooded animals comprising the administration of egg yolk, whole eggs, egg yolk protein (IgY fraction), or egg white derived from eggs produced in female avians hyperimmunized with the Stolle S-100 series vaccine.

In further specific preferred embodiments, the eggs or egg components derived from avians hyperimmunized with the Stolle S-100 vaccine are administered to animals on a high cholesterol diet. In other preferred specific embodiments, the effects on atheromatous lesions are obtained in the aorta and/or coronary artery.

In further preferred embodiments, a method is provided for lowering the levels of lipid deposits in a warm-blooded animal comprising administering to the animal egg or egg product from a hyperimmunized avian.

In further specific preferred embodiments a method is provided for lowering the levels of lipid deposits in the aorta of a warm-blooded animal comprising administering to the animal egg or egg product derived from female avians hyperimmunized with *Aerobacter aerogenes*.

In further preferred embodiments, a method is provided for the ingestion of eggs or egg products by a warm blooded animal without increasing the lipid deposits in the animal, comprising administering to the animal egg or egg product from a hyperimmunized avian.

In specific embodiments of the invention, a method is provided for the ingestion of eggs or egg products by a warm-blooded animal without increasing the levels of lipid deposits in the aorta of the animal, comprising feeding the animal eggs or egg products from a female avian hyperimmunized with the Group A or Group E bacterial antigen strains disclosed in Table 1 of the present specification.

In further specific preferred embodiments of the invention, a method is provided for the ingestion by a warm-blooded animal of eggs or egg products without increasing-lipid deposits in the liver comprising the ingestion of eggs or egg products derived from female avians hyperimmunized with the Group A, E, F, or G series of bacterial antigens, (Table 1 of the present specification).

In further preferred embodiments of the invention, a method is provided for the ingestion of eggs and egg fractions without increasing lipid levels or serum cholesterol in animals ingesting eggs or egg fractions compared to those levels found in animals ingesting equivalent amounts of normal untreated eggs, the method comprising ingesting eggs or egg products derived from hyperimmunized avians.

In further specific preferred embodiments of the present invention, a method is provided for the ingestion of eggs and egg fractions without increasing lipid levels in the aorta or liver of animals ingesting the eggs or egg fractions or without increasing serum cholesterol levels in animals ingesting the eggs or egg fractions to the levels found in animals ingesting equivalent amounts of normal eggs, comprising the ingestion by the animals of eggs or egg products derived from female avians hyperimmunized with *E. coli, Salmonella enteritidis, Pseudomonas aeruginosa, Klebsiella pneumoniae, Shigella dysenteriae, Strep. pyogenes* (Types 1, 3, 5, 8, 12, 14, 18 and 22), or Group E shown on Table 1 of the Applicants' specification.

Accordingly, in further preferred embodiments of the invention, vaccines comprising the specific individual effective bacterial antigens, groups of antigens, and subgroups of antigens, as described above and shown in Tables 1 and 2 of the present specification, are provided in vaccine form hyperimmunizing female avians to produce the eggs and egg fractions of the present invention.

In further preferred embodiments of the present invention, a method is provided for the production of eggs or egg products with the beneficial effects described above comprising the hyperimmunization of female avians with the specific bacterial antigens, groups, or subgroups described herein (supra, and Tables 1 and 2 of the present specification).

As used hereinafter, the tern "anti-cholesterolemic egg (s)" refers to the avian eggs of the present invention, said eggs produced by maintaining the animal producing said eggs in a hyperimmune state against a specific class of bacterial antigens, "anti-cholesterolemic antigen(s)." As used hereinafter the term "vaccine" refers to a suspension of bacteria or some antigenic part thereof which, when administered to an avian, results in the production of antibodies against said bacteria.

Examples of vascular disorders which may be treated with the anti-cholesterolemic eggs of the present invention include aging disorders such as an increase in the rigidity of vessels and an increase in the incidence wherein the large arteries become dilated and elongated, as well as a decrease in aneurysms which form in areas of encroaching arteriosclerotic plaques. Other aging-induced vascular damage which can be prevented or reversed with the anti-cholesterolemic eggs of the present invention is the increase in the thickness of the arterial intima, the reversal of gradual accumulation of smooth muscle cells, as well as a decrease in the accumulation of lipid content in the arterial wall.

Among the abnormal (i.e., non-aging induced) disorders of the vascular system which are preventable or reversible with the anti-cholesterolemic eggs of the present invention is arteriosclerosis, which includes both atheromatous and non-atheromatous forms. Among the non-atheromatous forms of arteriosclerosis treatable with the eggs of the present invention is focal calcification (also called Monckberg's sclerosis), which is common in the lower extremities, upper extremities, and the arterial supply of the genital tract in both sexes. Another disorder is focal calcification, which involves degeneration of the smooth muscle cells followed by calcium deposition. Another non-atheromatous form of arteriosclerosis is arterio-sclerosis which involves hyaline and general changes affecting both the intima and media of small arteries and arterials, particularly in the spleen, pancreas, adrenal, and kidney.

Importantly, the anti-cholesterolemic eggs of the present invention can be utilized for the treatment of atherosclerosis. This involves both the prevention and regression of the formation of fatty streaks, fibrous plaques, and complicated lesions, as described previously. Although it is probable that irreversible risk factors for atherosclerosis, such as male gender or genetic traits, might not be reversed with the eggs of the invention, the so-called reversible factor, however, may.

Thus, the anti-cholesterolemic eggs of the invention are useful in reducing the accumulation of lipids and preventing or reversing hypercholesterolemia or hypertriglyceridemia. Various forms of atherosclerosis can be treated.

Further, the anti-cholesterolemic eggs of the present invention are extremely valuable as a food source for egg protein. While avian eggs are known to be high in protein, conventional eggs, including the prior art eggs produced from immunized animals, have the undesirable characteristic of producing elevation in serum cholesterol upon consumption, even in normal healthy animals. The anti-cholesterolemic eggs of the present invention do not produce a marked elevation. Nor do they affect vascular lipid deposits as do untreated normal eggs.

In the process of this invention, the source animal includes any eggproducing member of the class Aves, preferably, but not limited to, domesticated chickens (genus *Gallus domesticus*). Alternatively, genera represented by turkeys, ducks, geese, and the like may be used as the source of the hyperimmunized eggs.

The invention is based on the discovery that when such avians are brought to a specific state of immunization by means of periodic booster administrations of a specific class of bacterial antigen, or a mixture of such antigens, the animal will produce eggs which, when consumed, do not elevate serum cholesterol to the levels found in animals consuming equivalent amounts of normal eggs, which lower lipid deposits in the aorta, which maintain lipid deposits in the aorta or liver, or which do not elevate hepatic or aortic lipid deposits to the levels observed in mammals ingesting equivalent amounts of normal eggs, and will, therefore, have beneficial properties in the treatment of vascular disorders. These are "anti-cholesterolemic" eggs. The beneficial egg properties are not produced by all avians that are simply immunized. That is to say, the induction of immune sensitivity alone is insufficient to cause the appearance of the aforementioned anti-cholesterolemic properties in eggs, as is shown by the fact that normal fowl eggs do not contain these properties, even though fowl have become sensitized against various antigens during normal immunization against fowl diseases.

Furthermore, the properties are not always present in eggs produced by fowl maintained in the immune state by booster injection. It is only in a specific hyperimmune state that the eggs produced have the desired effect. This special state is achieved only by administering periodic boosters with sufficiently high doses of specific bacterial antigens or mixtures of such antigens. The preferred dose range should be equal to or greater than 50% of the dosage necessary to cause primary sensitization of the avian. Having knowledge of the requirement for developing and maintaining a hyperimmune state, it is within the skill of the art to vary the amount of bacterial antigen administered, depending upon the avian genera and strain employed, in order to maintain the animal in the hyperimmune state.

In summary, the process comprises the following steps:

1. Selection of bacterial antigen or antigens.
2. Sensitization of avians by primary immunization.
3. Administering boosters of bacterial antigens of appropriate dosage to induce and maintain a hyperimmune state.
4. Collecting eggs from the animal during the hyperimmune state.
5. Testing anti-aging or anti-arteriosclerotic properties of eggs collected from said hyperimmune avian.

Step 1—The method of treatment is to immunize the avian with a specific bacterial vaccine. The avian responds by producing antibodies in the eggs against the bacterial species used for the immunization. Specific egg antibodies produced in response to the immunization result in the anti-cholesterolemic factors. It was not known prior to the present teaching that avian antibodies produced against certain bacterial species and found in the eggs of said avians have anti-cholesterolemic properties. Table 1, which gives the bacterial species composition of 14 different vaccines used to immunize chickens, demonstrates that polyvalent vaccine A comprises 26 different bacterial species or subtypes. This vaccine, known as the "Series 100" or "S-100" vaccine has also been described in U.S. Pat. Nos. 5,106,618, 5,128,127, 4,879,110, 5,194,255, and 4,956,349, all assigned to Stolle Research and Development Corporation. The results in Table 2 demonstrate that the eggs obtained from chickens immunized against polyvalent vaccine A contain the anti-cholesterolemic factor(s).

TABLE 1

Bacterial Species Composition of 14 Different Vaccines (A–N) Used to Immunize Chickens

| Bacteria | A | B | C | D | E | F | G | H | I | J | K | L | M | N |
|---|---|---|---|---|---|---|---|---|---|---|---|---|---|---|
| Staph. aureus | + | + | | | | | | | | | | | | |
| Staph. epidermidis | + | + | | | | | | | | | | | | |
| Strep. pyogenes, A. Type 1 | + | + | | | | | | | | | | | | |
| Strep. pyogenes, A. 3 | + | + | | | | | | | | | | | | |
| Strep. pyogenes, A. 5 | + | + | | | | | | | | | | | | |
| Strep. pyogenes, A. 8 | + | + | | | | | | | | | | | | |
| Strep. pyogenes, A. 12 | + | + | | | | | | | | | | | | |
| Strep. pyogenes, A. 14 | + | + | | | | | | | | | | | | |
| Strep. pyogenes, A. 18 | + | + | | | | | | | | | | | | |
| Strep. Pyogenes, A. 22 | + | + | | | | | | | | | | | | |
| Aerobacter aerogenes | + | | | + | + | | | | | | | | | |
| Escherichia coli | + | | | + | | + | | | | | | | | |
| Salmonella enteritidis | + | | | + | | | + | | | | | | | |
| Pseudomonas aeruginosa | + | | | + | | | | + | | | | | | |
| Klebsiella pneumoniae | + | | | + | | | | | + | | | | | |
| Salmonella typhimurium | + | | | + | | | | | | + | | | | |
| Haemophilus influenzae | + | | | | + | | | | | | | + | | |
| Strep. mitis | + | | | | + | | | | | | | | | |
| Proteus vulgaris | + | | | | | + | | | | | | | + | |
| Shigella dysenteriae | + | | | | | + | | | | | | | | + |
| Diplococcus pneumoniae | + | | + | | | | | | | | | | | |
| Propionibacter acnes (anaerobe) | + | | + | | | | | | | | | | | |
| Strep. sanguis | + | | | + | | | | | | | | | | |
| Strep. salivarius | + | | | + | | | | | | | | | | |
| Strep. mutans | + | | | + | | | | | | | | | | |
| Strep. agalactiae | + | | | + | | | | | | | | | | |

TABLE 2

Autopsy Scores and Cholesterol Concentrations in Rabbits Fed Eggs Obtained from Chickens Hyperimmunized Against 14 Different Bacterial Vaccines

| | No. of Rabbits & | Autopsy Score | | Cholesterol Levels | |
|---|---|---|---|---|---|
| | | | | Serum | Liver |
| Vaccine | Rabbit Group | Aorta | Liver | (mg %) | (mg/G) |
| Neg. Cont.[a] | 4; not given | 0 | 0 | 283 | 7.0 |
| Pos. Cont.[b] | 2; 38-8 | 5 | 5 | 764 | 9.3 |
| A | 4; 38-16 | 0 | 0 | 796 | 12.4 |
| B | 3; 38-12 | 5 | 5 | 560 | 12.9 |
| C | 1; 38-13 | 5 | 5 | 1600 | 22.5 |
| D | 2; 38-14 | 5 | 5 | 1210 | 28.5 |
| E | 1; 38-15 | 0 | 0 | 428 | 8.9 |
| F | 3; 38-19 | −2 | 0 | 271 | 7.9 |
| G | 3; 38-20 | 1 | 0 | 388 | 11.9 |
| H | 2; 38-21 | 2 | 3 | 495 | 13.9 |
| I | 2; 38-22 | 4 | 3 | 551 | 13.3 |
| J | 3; 38-23 | 4 | 3 | 574 | 12.3 |
| K | 2; 38-24 | 5 | 5 | 472 | 25.9 |
| L | 2; 38-25 | 5 | 5 | 683 | 27.9 |
| M | 3; 38-26 | 5 | 5 | 706 | 23.6 |
| N | 3; 38-27 | 2 | 5 | 868 | 35.8 |

[a]Rabbits not fed eggs.
[b]Rabbits fed eggs from non-hyperimmunized chickens.
[c]O is equivalent to negative control; 5 is equivalent to positive control.

Step 2—Antigens can be administered by any method which causes sensitization. The preferred method of immunization is by intramuscular injection. The preferred method of administration of the antigens to chickens was in the breast muscle. The dosage is preferably 1–5 mg of the mixed bacterial vaccine. Repeated immunizations are given at intervals, preferably two-week, over a suitable period of time, preferably six months.

It can be determined whether or not the avian has become sensitive to the antigen. There are a number of methods known to those of skill in the art of immunology to test for sensitivity. *Methods in Immunology and Immunochemistry*, Williams, C. A., Chase, W. N., Academic Press, N.Y., London (Vols. 1–5) (1977). The appearance of egg antibodies after immunization with the vaccine is indicative of sensitivity. The minimum dose of antigen necessary to induce hypersensitivity depends on the type of antigen used.

Step 3 involves the induction and maintenance of the hyperimmune state. This state is induced by repeated booster administration of an appropriate dosage at fixed-time intervals, preferably two-week intervals over a six-month period of time where polyvalent bacterial agents are employed. Moreover, the booster administration must not induce a state of immune tolerance. This will cause the animal to pass from a hyperimmune state to a state of immune tolerance to the antigen, in which case the animal will cease to produce eggs with the beneficial properties.

It might also be possible, for example, to use a combination of different immunization procedures, i.e., intramuscular injection for primary immunization and intravenous injection for booster injections, etc. Many different combinations of immunization might be employed by those skilled in the arts to: (1) sensitize and (2) induce the hyperimmune state.

Step 4 involves collection and processing of the eggs. If the eggs are to be processed into dried egg powders, freeze-drying (lyophilization) is the preferred method. Whole eggs can also be used, as well as eggs that have been separated into egg yolks, egg white, and IgY protein fraction.

Immune egg yolk IgY protein fraction is prepared by the CAPS (caprylic acid) method as follows: S-100 yolk was diluted 7.5 fold with deionized water then diluted 1:1 with 0.06M acetate buffer, pH 5. One percent caprylic acid was blended in. The preparation was allowed to stand for 2 hours for separation of the aqueous (bottom) layer and the flocculate (top) layer. After phase separation, the immunoglobulins are present in the bottom aqueous layer and the majority of other components, including most lipoproteins, lipids, cholesterol, and yolk enzymes, are in the lipidic top flocculate layer. The aqueous phase then was adjusted to neutral pH and diafiltered and concentrated using 100K hollow fiber ultrafiltration membrane, Amicon H5P100-43. The retentate, a fraction which exhibits antibody activity against antigens in the S-100 vaccine is the IgY protein fraction. The Roese-Gottlieb (AOAC) method used for fat determination was unable to detect any fat in the sample, indicating less than 0.01% fat.

The yield, concentration, and purity of the obtained pure IgY product can be determined by any of the standard methods known to those of ordinary skill in the art. For example, suitable methods include those described in Harlow et al, Antibodies: *A Laboratory Manual* pp. 553–612+ 636–681 (1988), incorporated herein by reference.

Step 5 is to test the anti-cholesterolemic and vascular disorder treatment properties of the eggs and egg products. A battery of research techniques can be used to test the effects of the hyperimmune eggs on the vascular system of animals. Preferably, suitable strains of rabbits are used as the test animal. Such animals, being susceptible to hypercholesterolermia, hyperlipidemia and atherosclerosis, are a well-established animal model for these disease entities in man. Duff, G. L., et al, *J. Exper. Med.* 89:611–630 (1949), at 612. These tests include in all cases feeding said test rabbit a diet which comprises hyperimmune eggs (with a control comprising animals with a diet containing normal eggs and another control comprising animals with an egg-free diet). After a predetermined period of time, preferably feeding rabbits one egg a day for 90 days with the egg being mixed with the drinking water of the rabbit, the rabbits are sacrificed and autopsies performed. The livers and aortas of the rabbits are dissected and examined for fatty deposits. Samples of these tissues are examined by standard histological methods to evaluate the level of lipid deposits in both the liver and aorta. A scoring system can be used to compare the degree of lipid deposits observed in the livers and aortas among the treatment and control groups. The following scoring system was preferred. The liver and aortas of each rabbit are dissected and given a score of 0–5, depending upon the amount of lipid deposits that were observed. A score of 0 is equivalent to a control that was not fed eggs, and a score of 5 is equivalent to controls fed normal chicken eggs. Histological sections are evaluated by the same criteria. The average score of each group of animals is then calculated. According to this scoring system, a mean score of 0 would indicate complete prevention of lipid deposits in the liver and aorta due to egg cholesterol in the diet, whereas a score of 5 would indicate no protection. Scores between 0 and 5 would indicate intermediate levels of protection, 1 being greater than 2, etc. In addition to this, the quantity of lipid in the blood and in liver and heart tissues can be measured using standard biochemical methods.

The histological examination of blood vessels and liver can include any of the following techniques: scanning electron microscopy of the endocardial surfaces of the heart searching for endothelial damage; transmission electron microscopy of vessels searching for lipid droplets, endothelial degeneration, lipid presence in thome cells, or a tendency of fibrin or platelets to adhere to the lumenal surface of endothelial cells; histological analyses of hearts searching for lipid, e.g., cholesterol; demonstration of lipids with oil-soluble dyes such as oil red or Sudan black in sections of frozen tissues, or the presence of enzymes, especially cytochrome oxidase.

The present invention is based in part on the discovery that anti-cholesterolemic eggs have beneficial properties on the cardiovascular system. For example, it has been discovered that in hearts of female rabbits which have been fed a steady diet of anti-cholesterolemic eggs, the endothelial cells of the heart are protected against extensive endothelial damage of varying extent and severity observed in rabbits fed normal eggs with their well known high cholesterol content. In the latter rabbits, craters or holes are present where one or more cells have degenerated and detached, whereas in anti-cholesterolemic hyperimmune egg-fed rabbits, these were not present. Transmission electron microscopy of both populations of rabbits show major differences in the blood vessels. Significant pathological features of blood vessels in control hearts include large lipid droplets, endothelial degeneration, multiple small lipid vacuoles, single or multiple large lipid droplets filling the cytoplasm of endothelial cells, foam cells latent with lipid, and a strong tendency of fibrin platelets to adhere to the lumenal surface of endothelial cells. All of the aforementioned derangement accompany the pathogenesis of atherosclerosis. These derangements are not found in blood vessels from representative areas of rabbit populations that are on a steady diet of hyperimmune eggs. Histological sections of hearts from the rabbits fed the hyperimmune eggs or milk and of rabbits fed control eggs or milk show that lipid is present in the lumena of some blood vessels of control hearts, and cardiac muscle fibers of control hearts are filled with lipid. Coronary blood vessels from rabbits fed on hyperimmune eggs lack the atherosclerotic lipid deposits which are observed in control vessels. These results demonstrate that anti-cholesterolemic eggs slow and/or repress the pathogenesis of arteriosclerosis and aging of the heart. The same tests on rabbit populations demonstrate that diets incorporating the hyperimmune eggs of this invention not only result in a reduction of the concentrations of serum cholesterol, triglycerides, and low-density lipoproteins, all of which are key factors associated with cardiovascular disease, but also fail to bring about the increase in said serum lipids generally observed in humans (and other warm-blooded animals) who consume eggs.

The eggs of the invention can be provided in any amount which effects or maintains the reversal of vascular disorders in warm-blooded animals.

The same amounts can be utilized in normal subjects when operating in a preventive mode. The whole eggs or egg yolks can be incorporated into any food product, as long as the food product is not treated at a temperature which is too elevated and which would thereby inactivate the beneficial properties of the product.

By the term "anti-cholesterolemic egg or fraction thereof" is intended an egg or egg fraction containing a factor or factors that produce the results described in detail supra. Specifically, the ingestion of the egg fractions, whole eggs, or factor(s) contained therein, produced by hyperimmunizing female avians with the specific bacterial antigens, such as those described herein, produce the specific effects. The effects described include the lowering of lipid deposits in the aorta, the maintenance of lipid deposits in the aorta or liver or the relatively lower elevation of lipid levels in the aorta or liver or in the serum cholesterol compared to the levels found in animals ingesting equivalent amounts of untreated eggs. The term or phrase also includes eggs or egg fractions or factors which reduce the development of atheromatous lesions. The term or phrase also refers to eggs, egg fractions, or factors which reduce the severity of atheromatous lesions in aorta or coronary artery. The term or phrase may also be extended and would be understood to include the effects related to those specifically disclosed herein. That is, to all the effects, biochemical and biological, which, in view of the results disclosed herein and the physiological knowledge of vascular disease in a warm-blooded animal, would be expected. By "anti-cholesterolemic antigen" is intended, antigens, which when used to hyperimmunize an avian, produce the anti-cholesterolemic eggs or egg fractions.

By the term "untreated" or "normal" eggs for the purpose of the present invention in intended control eggs that have been derived from non-hyperimmunized chickens. These eggs would include those that are routinely commercially available or which have been collected in the field and which were not subjected to experimental treatments by the hand of man other than those routinely applied to eggs and especially eggs intended to be used as foodstuffs.

By "administration" is intended any manner of entry into the body that is effective to produce the anti-lipid, anti-cholesterol effects. The preferred method for the egg and egg products is oral ingestion. However, the factors may also be administered by parenteral or intravenous routes, intramuscularly, or subcutaneously. The skilled artisan would be aware of the various routes of administration.

By "high cholesterol diet" is intended the intake of dietary cholesterol or food products producing cholesterol metabolically, in excess of the cholesterol normally needed for proper biological function of the animal.

By "egg product" is intended the processed form of the egg to be used in the future, for example freeze-drying, and other known methods of egg preservation.

By "egg component" or "egg fraction" is intended the yolk, white or IgY protein fraction as described herein.

Having now generally described this invention, the same will be further described by reference to certain specific examples which are provided herein for purposes of illustration only and are not intended to be limiting unless otherwise specified.

EXAMPLE 1

Results of Ingestion of Eggs Produced by Hyperimmunization with Various Bacterial Antigens: serum cholesterol, lipid deposits in liver and aorta Five chickens were immunized against polyvalent bacterial vaccine A (cf., Table 1). This vaccine contains all of the S-100 strains.

Bacterial cultures were obtained from the American Type Culture Collection (ATCC). They were reconstituted with medium and incubated overnight at 37° C. About half of each bacterial suspension was used to inoculate one liter of broth; which was cultured at 37° C. The remaining suspension was stored in sterile glycerol at −20° C. After good growth was apparent, bacteria were harvested by centrifugation of 14,000× g for 20 min. The pellet of bacteria was washed by repeated (3X) suspension in saline and reisolation by centrifugation. Washed pellets were suspended in a small volume of distilled water, and bacteria were heat-killed by maintenance at 80° C. overnight. Heat-killed bacteria were lyophilized and stored in sterile vials at −20° C.

An amount of bacterial antigen sufficient to immunize up to 10 adult female chickens was prepared as follows. About 350 mg of mixed bacterial powder was suspended in 1 liter of sterile saline to a concentration of approximately $202 \times 10^8$ bacterial cells/ml. saline ($A_{600}$=1.0). One ml. of this mixture was injected into each chicken. Repeated immunizations were given at two-week intervals over a six-month period of time.

Eggs were collected from chickens beginning one month after the first immunization. Rabbits, which are known to be a valid model of human arteriosclerosis (Duff et al supra), were fed one egg per day for 90 consecutive days. The eggs were mixed with the drinking water of the rabbit. Three rabbits were fed the eggs obtained from the chickens immunized against polyvalent vaccine A. Six additional rabbits were used as controls. One control group of three rabbits were fed eggs from non-immunized chickens, and the other control group of three rabbits was fed the same daily ration of rabbit food, but no eggs. After 90 days, the rabbits were sacrificed and autopsies were performed. The livers and aortas of the rabbits were dissected and examined for fatty deposits. Samples of these tissues were examined by standard histological methods to evaluate the level of lipid deposits in both the liver and aorta. Serum and liver lipid concentrations were estimated by standard chemical analysis.

The results shown in Table 2 show that the eggs obtained from chickens immunized against the polyvalent bacterial vaccine A contain the anti-cholesterolemic/anti-lipid factor (s).

Table 2 also shows results of further subdividing the A group of antigens and producing immune eggs fed to test rabbits.

Five chickens were immunized with each of vaccine groups B through E listed in Table 1, according to the protocol described in Example 1 above. Eggs obtained from these chickens were evaluated in rabbits according to the same procedure described above in Example 1. Results from these rabbit experiments are summarized in Table 2. The anti-cholesterolemic effect is absent in rabbits fed eggs of vaccine groups B, C, and D, but the anti-cholesterolemic effect was present in rabbits immunized against bacterial vaccine group E.

Groups of five chickens each were immunized with each of the nine individual bacterial species included in vaccine E of Table 1, according to the protocol of Example 1. Eggs from these chickens were fed to rabbits according to the same experimental protocol described above in Example 1. The results from this series of experiments are summarized in Table 2.

EXAMPLE 2

Results of Ingestion of Egg Fractions from Hyperimmunized Avians: serum cholesterol, plaque, organ cholesterol Thirty-five New Zealand White (NZW) Rabbits were used in this study. All were specific pathogen free (SPF) females. They were obtained when about six weeks old from a licensed commercial vendor. They were housed (one/cage) throughout the study in the vivarium of the Structural Research Center, 120 Novatan Road, Mobile, Ala. 36608. The controlled environment provided rabbits with twelve hours of light and twelve hours of darkness during each twenty-four hour day.

Rabbits were divided into seven groups of five rabbits each. Beginning body weights, body weights at sacrifice, splenic weights, and adrenal weights of each rabbit in each group were recorded.

The duration of the study was 14 weeks. Baseline data (body weights and two serum cholesterol values) were obtained during weeks 1 and 2 as the rabbits were allowed to stabilize in their new environment. In the remaining 12 weeks, each group was treated as follows: Group I, High Cholesterol Diet plus Immune Egg Yolk; Group II, High Cholesterol Diet plus Water; Group III, High Cholesterol Diet plus Immune Whole Egg; Group IV, High Cholesterol Diet plus Immunoglobulin Y Egg Yolk Protein; Group V, High Cholesterol Diet plus Control Whole Egg; Group VI, High Cholesterol Diet plus Immune Egg White; and Group VII, Standard Diet plus Water.

Following preparation and prior to use, all fractions were maintained in a deep freeze at −10 degrees Fahrenheit. Products were thawed just prior to use.

Immune eggs were obtained from chickens vaccinated fortnightly with Stolle Research & Development Corporation's proprietary multivalent bacteria known as the "Series 100" or "S-100" vaccine. The eggs showed high titers of antibodies to the antigens in the vaccine, as determined by ELISA. Fresh immune eggs were cracked, blended, placed in plastic bags in 250 mL aliquots and frozen. Immune yolks and whites were separated, diluted to a similar volume as whole eggs (50 mL per egg), blended, placed in plastic bags in 250 mL aliquots and frozen. Control eggs were obtained from ordinary commercial sources and prepared exactly the same as whole immune eggs. The products were provided in sterilized drinking bottles as the only source of fluid. The products are stable indefinitely when stored in the frozen state. No other drugs or biologics were utilized as a part of this trial.

Rabbits received fresh liquid daily in sterilized bottles with drinking tubes. Each rabbit received an equivalent of one egg/day mixed in 500 mL of water. Immunoglobulin Y Yolk Protein Concentrate was also prepared and added to 500 mL of water at the equivalent of 1 egg/day.

Immune egg yolk protein IgY fraction is prepared by the CAPS (caprylic acid) method as follows: S-100 yolk was diluted 7.5 fold with deionized water then diluted 1:1 with 0.06M acetate buffer, pH 5. One percent caprylic acid was blended in. The preparation was allowed to stand for 2 hours for separation of the aqueous (bottom) layer and the flocculate (top) layer. After phase separation, the immunoglobulins are present in the bottom aqueous layer and the majority of other components, including most lipoproteins, lipids, cholesterol, and yolk enzymes, are in the lipidic top flocculate layer. The aqueous phase then was adjusted to neutral pH and diafiltered and concentrated using 100K hollow fiber ultrafiltration membrane, Amicon H5P100-43. The retentate, a fraction which exhibits antibody activity against antigens in the S-100 vaccine is the IgY protein fraction. The Roese-Gottlieb (AOAC) method used for fat determination was unable to detect any fat in the sample, indicating less than 0.01% fat.

Due to the large volume of IgY protein required for the study, four CAPS procedures were performed using 190, 204, 219, and 211 S100 eggs. All retentates were combined and total volume was adjusted to the approximate antibody titer of starting yolk, then bagged in 280-ml aliquots and stored at −20° C. until use.

The IgY yolk protein fraction can also be prepared by any one of the methods disclosed for large-scale preparation of the IgY fraction in co-pending application Ser. No. 08/045, 061 incorporated herein by reference.

Liquid consumption for each rabbit was recorded daily. The amount of solid food consumed weekly by each rabbit was also recorded.

The standard diet was Purina High Fiber Rabbit Chow. The high-cholesterol diet contained 0.25% cholesterol. It was prepared as described by (Rodman, N. F. et al., *Scanning Electron Microscopy* 3:835–842 (1979)). The diet contained Purina High Fiber Rabbit Chow (94%), cholesterol (0.25%), and corn oil (5%). The diet was mixed by blending 4700 g of the Purina Chow, 12.5 g cholesterol, and 250 g corn oil. Pure ethyl ether (IL) was used to dissolve the cholesterol and to thin the corn oil. The combination was then poured onto the chow and thoroughly mixed into the chow. After the ether had evaporated, the chow had a homogeneous coating of oil and cholesterol. The diet was known to cause predictable increases in serum cholesterol and development of atherosclerotic lesions of the aorta and coronary arteries. The diet served as the sole source of nutrition.

Following the baseline period, blood was obtained every four weeks from an ear artery of each rabbit, using aseptic techniques. The serum was separated and stored frozen until assayed for serum cholesterol according to the procedure of Zlatkis et al. (Zlatkis, A. et al., *Journal Laboratory & Clinical Medicine* 41:486–492 (1953)). Weights of rabbits were recorded at biweekly intervals during treatment. Body weights showed that the rabbits experienced normal growth.

All rabbits were sacrificed by injecting an overdose of sodium pentobarbital (65 mg/mL) into an ear vein. A necropsy was performed immediately. Organs were removed and inspected for gross lesions. Hearts (with coronary arteries and cardiac valves), aortas, spleens, suprarenals, and livers were removed at necropsy, processed by standard methods, sectioned, stained, and studied microscopically. The spleen and two suprarenal glands were weighed to the nearest milligram, and the ratio of organ weight to body weight was found. All organs were prepared by standard methods for microscopic study. The initial fixative was cold (50° C.) 1% glutaraldehyde and 1% paraformaldehyde in Millonig's Phosphate buffer (pH 7.3). Atherosclerosis evaluation was performed on a blind basis by gross examination and light microscopy with histochemical staining.

At least five representative segments of the aorta were embedded in paraffin for sectioning, staining, and microscopic study. Segments of the aorta were taken as it emerged from the base of the heart, the aortic arch, the upper thoracic aorta, the middle thoracic aorta, and the lower thoracic aorta. Sections were made through at least six levels of the heart to show the coronary arteries. The bicuspid valve was included in some of the sections. One or more frozen sections were made of representative hearts, and stained with Oil Red-O for lipids. Sections were also made of paraffin embedded blocks of the liver, adrenal, and spleen; they were stained with H&E. Ten sections of the aorta and ten sections of the heart were examined microscopically and scored. For scoring the aorta and coronary artery, the arterial lumen was divided into four quadrants and numbered: Quadrant 1, Top left; Quadrant 2, Top Right; Quadrant 3, Bottom Right; and Quadrant 4, Bottom Left. The Degree of Severity of Plaque (Plaque Score) in a cross-section of an artery was determined as follows: 0=no plaque; 1 =plaque in only one quadrant; 2=plaque in 2 quadrants; 3=plaque in 3 quadrants; 4=plaque in 4 quadrants; and 5=continuous plaque in all 4 quadrants. Foam cells only were sometimes present. They were considered to represent plaque during lesion histogenesis.

Thoracic aortas were photographed under a stereomicroscope after staining with Sudan IV. Photomicrographs were taken of representative sections of aortas, coronary arteries, bicuspid valves, livers and spleens. The percent sudanophilia of each aorta was determined by automated image analysis. Values represented the stained plaque in two, 100 sq mm segments of aorta.

RESULTS AND DISCUSSION

Body weights were taken at biweekly intervals throughout the study, and they showed that rabbits in all groups experienced normal weight gain expected for healthy rabbits. Final body weights for rabbits on control whole eggs, immune whole eggs, or immune egg components did not differ significantly.

The daily liquid consumption, the amount of solid food consumed weekly, and the total quantity of liquid and solid food consumed/rabbit/group during treatment were recorded. No significant differences were noted.

Rabbits in groups that were challenged with a high-cholesterol diet developed hypercholesterolemia and their thoracic aortas showed atherormatous lesions of various degrees. Rabbits on a standard diet did not develop hypercholesterolemia. Some, however, had atheromatous lesions in the coronary artery. In rabbits, as in humans, lesions may develop without known cause.

Figure 1:
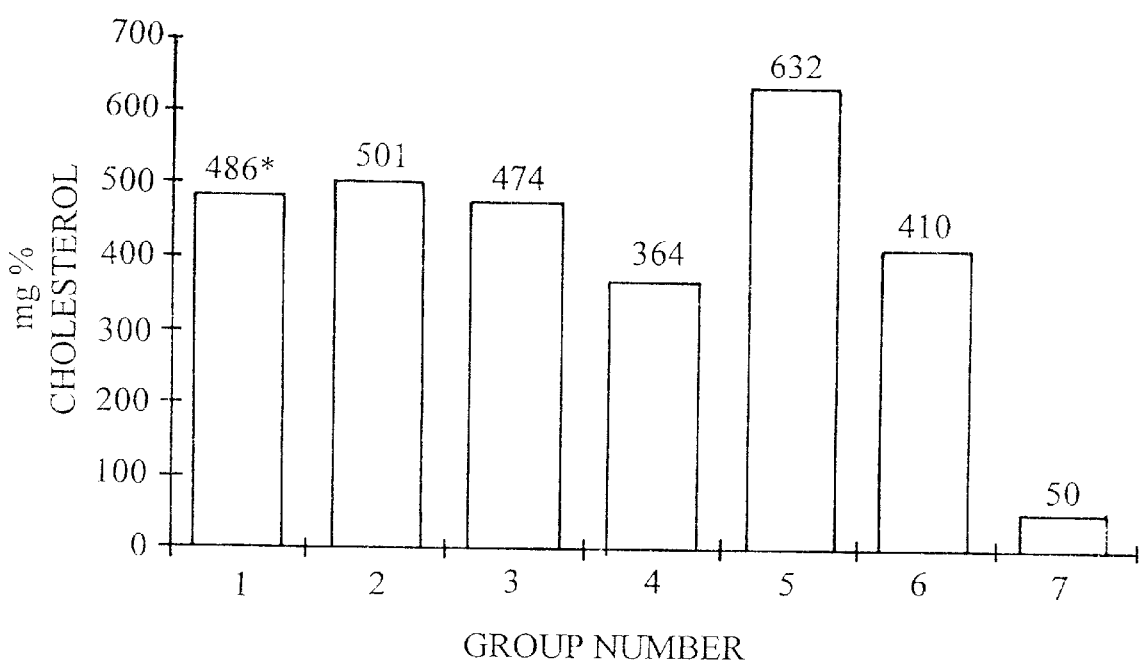
FIG. 1 shows final mean serum cholesterol values for each group of NZW rabbits. The horizontal axis shows the group number and the vertical axis shows the milligram percent of cholesterol. An explanation of the groups is provided underneath the figure. The dietary regimen is described in Example 2 of the present specification.

All rabbits on high-cholesterol diets plus immune whole eggs, immune egg yolks, immune egg whites, or immune egg yolk IgY had lower final serum cholesterol values than rabbits on HCD plus water or control whole eggs (FIG. 1). The greatest effect was with the yolk protein fraction and with the egg white fraction.

Compared to the final serum cholesterol levels in animals ingesting a high-cholesterol diet plus untreated whole eggs, the final serum cholesterol levels were as follows: egg yolks, 23% lower; high-cholesterol diet without any eggs, 21% lower; whole eggs, 25% lower; egg yolk IgY protein, 42% lower; and egg white, 35% lower. Compared to the serum cholesterol levels in animals ingesting a high-cholesterol diet but not further ingesting eggs, the final serum cholesterol values were as follows: egg yolks, 3% lower; whole eggs, 5% lower; egg yolk IgY protein, 27% lower; and egg white, 18% lower.

The histopathologic findings for individual specimens addressed the percent of sudanophilia/200 sq. mm of aorta/rabbit and the severity of aortic and coronary plaque in each histological section that was examined. The percentage of plaque was determined by automated image analysis (FIG. 2). Aortas of rabbits in Group 5 (control whole eggs plus HCD) had the highest percentage of plaque followed in decreasing order by rabbits in Group 1 (immune egg yolks plus HCD), Group 4 (IgY plus HCD), Group 6 (immune egg whites plus HCD), Group 3 (immune whole eggs plus HCD), and Group 2 (water plus HCD). The greatest decreases were obtained with immune whole eggs, immune yolk protein fractions, and immune egg white fractions.

Compared to the percentage of plaques in animals on a high-cholesterol diet and consuming untreated whole eggs, the percentage of plaque was as follows: egg yolks, 15% lower; high-cholesterol diet without ingestion of eggs, 47% lower; whole eggs, 38% lower; egg yolk IgY protein, 29% lower; and egg white, 29% lower.

Results of another study (not shown) showed that in the absence of a high-cholesterol diet, the aortas of rabbits fed immune whole eggs did not contain significant sudanophilic plaque. In contrast, aortas of rabbits fed control whole eggs were about 25% sudanophilic. Therefore, immune whole eggs prevented plaque formation even under normal dietary conditions.

FIG. 3 shows that the degree of severity of atheromatous lesions in aortas was greatest for rabbits in Group 5 that received control whole eggs plus HCD. Immune whole eggs, immune egg yolks, immune egg whites, and IgY reduced the degree of atheromatous lesions in aortas. Whereas control whole eggs elevated the severity, all of the immune fractions reduced the severity relative to control eggs, particularly the immune egg white.

Compared to the degree of severity of lesions in animals ingesting a high-cholesterol diet plus normal untreated whole eggs, the degree of severity is as follows: egg yolks, 26% lower; high-cholesterol diet without any eggs, 35% lower; whole eggs, 26% lower; egg yolk IgY protein, 27% lower; and egg whites, 36% lower.

FIG. 4 shows the severity of lesions in the coronary artery. Coronary arteries of rabbits in Group 2 (water plus HCD) and Group 5 (control whole eggs plus HCD) had identical severity scores (the highest for this study). Coronary arteries of rabbits in Group 3 (immune whole eggs plus HCD) and in Group 7 (water plus standard diet) also had identical severity scores (the lowest for this study). These data show that control whole eggs did not promote atheromatous lesions in coronary arteries above the level found with HCD alone. The data also show that control whole eggs did not prevent or lower the severity of coronary lesions. On the other hand, the data in FIG. 4 show that immune whole eggs, in marked contrast to control whole eggs, blocked the effects of the HCD and prevented coronary lesions. Immune egg yolks, IgY from immune egg yolks, and immune egg whites also reduced the severity of atheromatous lesions in the coronary arteries. Compared to the degree of severity of lesions in animals fed a high-cholesterol diet either with or without eggs, the degree of severity was as follows: egg yolks, 65% lower; whole eggs, 72% lower, egg yolk IgY protein, 53% lower; and egg whites, 36% lower. Whole eggs, in fact, lowered the degree of severity to the degree found in animals fed a standard diet.

Microscopically, livers, spleens, and heart valves of rabbits on immune whole eggs plus HCD or immune egg components plus HCD contained less cholesterol than corresponding organs of rabbits on control whole eggs plus HCD.

FIG. 5 summarizes results shown in FIGS. 1–4.

EXAMPLE 3

Average splenic weights and splenic weight/body weight ratios were highest for rabbits in Group 6 that received immune egg whites (2886 mg; 0.702 ratio), and for rabbits in Group 1 that received immune egg yolks (2658 mg; 0.702 ratio). Average splenic weights and splenic weight/body weight ratios were smaller for rabbits in Group 3 that received immune egg whites (1963 mg; 0.544 ratio) than for rabbits in Group 5 that received control egg whites (2435 mg; 0.706 ratio). Rabbits in Group 4 on IgY had the lowest average splenic weight (1575 mg; 0.45ratio) followed by rabbits in Group 7 that received water plus standard diet (1596 mg; 0.45 ratio).

Differences in splenic weight have clinical significance. IgY from immune egg yolks checked splenic enlargement in rabbits challenged with a high-cholesterol diet. IgY, therefore, has potential for use in preventing splenic hypertrophy and rapture in patients with either dietary or genetic hyperlipidemia. Other conditions that cause splenomegaly, such as malaria and sickle cell disease or trait (Yang, Yih-Ming et al., *American Journal of Hematology* 40:110–116 (1992)), may benefit from IgY.

Immune whole eggs stimulated splenic enlargement to a lesser degree than immune egg whites or immune egg yolks. Histologically, the chief target of stimulation in the spleen appears to be macrophages which are triggered to phagocytose cholesterol. The uptake of cholesterol by macrophages lowers serum cholesterol to some degree. It remains to be determined if the macrophages metabolize cholesterol for excretion. In an earlier pilot study with rabbits on regular diet and immune whole eggs, it was noted that splenic macrophages were stimulated and hypercholesterolemia did occur when rabbits were challenged with a high-cholesterol diet. Immune whole eggs consumed daily could possibly maintain splenic macrophages in a state of readiness to clear blood of excess lipids. Control eggs also promoted splenic enlargement, but the hypertrophy was associated with focal fibrosis, a condition that was not observed in spleens of rabbits on immune whole eggs or immune egg components.

Average weights of suprarenal glands and adrenal gland weight/body weight ratios were highest for rabbits in Group 3 on immune whole eggs (972 mg; 0.27 ratio), Group 6 on immune egg whites (900 mg; 0.25 ratio), and Group 5 on control whole eggs (878 mg; 0.26 ratio). It was concluded that weights of adrenal glands in all groups of rabbits on high-cholesterol diet were significantly increased. The spleen filters blood of worn-out red cells, removes excess lipids, and produces lymphocytes. In comparison, suprarenal glands produce steroid hormones in their cortical tissue, and catecholamines in their medullary tissue. The cortical tissue (chiefly the zona fasciculata) requires cholesterol for the synthesis of steroid hormones which it removes from the blood that passes through the gland. Adrenal cortical hormones are concerned chiefly with salt metabolism (mineralocorticoids form the zona glomerulosa) and sugar metabolism (glucocorticoids from the zona fasciculata). Weak sex hormones are also produced in the zona reticularis. It is interesting that the average weight for adrenal glands was greatest in the group of rabbits on immune whole eggs. It is not known if an increase in hormone production paralleled the increase in weight.

EXAMPLE 4

All S100 whole eggs and S100 egg components exhibited significant anti-*Salmonella enteritidis* ELISA activity as illustrated in Table 3. Tables 4, 5 and 6 show captylic acid content, fatty acid profile and protein recoveries of S100 yolk components after CAPS and ultrafiltration.

Anti-*Salmonella enteritidis* titer in S100 egg is determined by ELISA method. Egg protein was determined using Pierce Micro BCA Protein Assay method. Levels of caprylic acid and other fatty acids were measured as methyl esters and assayed using a Hewlett-Packard Series II 5890 Gas Chromatograph with 5971A Mass Selective Detector.

TABLE 3

Protein and ELISA of S100 and Control Egg Products

| Egg Products | Protein (mg/ml) | ELISA (%) | ELISA Protein | Caprylic** Acid (mg/ml) |
|---|---|---|---|---|
| Control Whole Egg | 118.15 | 0.40 | 0.00 | N/A |
| S100 Whole Egg | 117.66 | 22.70 | 0.19 | N/A |
| S100 Yolk | 136.83 | 70.90 | 0.52 | N/A |
| Diluted* S100 Egg Yolk | 67.15 | 34.30 | 0.51 | N/A |
| S100 IgY Protein | 15.58 | 31.70 | 2.03 | 0.2 |
| S100 Egg White | 94.63 | 0.00 | 0.00 | N/A |
| Diluted* S100 Egg White | 74.44 | 0.00 | 0.00 | N/A |

*Egg yolk and white samples were diluted to whole egg volume with sterilized deionized water.
**Caprylic acid content determined using GC/MS method.
N/A: Not Analyzed.

TABLE 4

Caprylic Acid Content in Phase-Separation and Ultra-filtration Products, Means of Four CAPS Extractions

| | Volume (ml) | Caprylic Acid Content (mg/ml) |
|---|---|---|
| Yolk Homogenate* | 51,897 | 7.8 |
| Aqueous Phase | 47,868 | 1.0 |
| Flocculate Phase | 3,359 | 68.5 |
| Retentate (IgY protein) | 5,974 | 0.2 |

*After addition of 1% caprylic acid.

TABLE 5

Profile of Fatty Acids from S100 Egg Yolk Phase Separation and Ultrafiltration Products

| | % Area Counts | | | | | | |
|---|---|---|---|---|---|---|---|
| | 8:0** | 16:0 | 16:1 | 18:0 | 18:1 | 18:2 | 20:4 |
| Yolk Homogenate*** | 32.1 | 20.3 | 0.0 | 7.4 | 29.1 | 11.1 | 0.0 |
| Aqueous | 100.0 | 0.0 | 0.0 | 0.0 | 0.0 | 0.0 | 0.0 |
| Precipitate | 19.9 | 21.5 | 2.0 | 8.9 | 32.3 | 13.3 | 1.9 |
| Retentate* | 100.0 | 0.0 | 0.0 | 0.0 | 0.0 | 0.0 | 0.0 |

*IgY protein; retentate obtained through diafiltration and concentration using 100 K ultrafilter (Amicon).
**Caprylic acid.
***After addition of 1% caprylic acid.

TABLE 6

Protein Recovery & ELISA of S100 Yolk After CAPS & Ultrafiltration

| Sample | Protein (mg/ml) | Volume (ml) | T Prot. (mg) | Yield (%) | ELISA (%) | ELISA/Protein |
|---|---|---|---|---|---|---|
| Fresh S100 Yolk Batch #1 | 151.28 | 3,110 | 470,481 | — | 58.00 | 0.38 |
| 15X Yolk in .06 M Acetate | 10.87 | 46,500 | 505,362 | 100.00 | 81.00 | 7.45 |
| 15X Yolk in .06 M Ac. 1% Cap. | 12.72 | 46,965 | 597,395 | 118.21 | 83.40 | 6.56 |
| Filtrate/Aqu. Layer Combined | 2.00 | 43,670 | 87,340 | 17.28 | 1.70 | 0.85 |
| 100K Permeate | 0.08 | 126,795 | 10,144 | 2.01 | 0.02 | 0.23 |
| 100K Retentate | 15.37 | 5,205 | 80,001 | 15.83 | 20.5 | 20.01 |
| Fresh S100 Yolk Batch #2 | 133.84 | 3,350 | 448,364 | — | N/A | N/A |
| 15X Yolk in .06 M Acetate | 10.75 | 50,250 | 539,987 | 100.00 | 81.60 | 7.59 |
| 15X Yolk in .06 M Ac. 1% Cap. | 7.91 | 50,752 | 401,347 | 74.33 | 68.70 | 8.69 |
| Filtrate/Aqu. Layer Combined | 1.93 | 47,190 | 91,077 | 16.87 | 2.89 | 1.50 |
| 100K Permeate | 0.21 | 135,270 | 27,886 | 5.16 | 0.03 | 0.13 |
| 100K Retentate | 15.20 | 5,730 | 87,096 | 16.13 | 39.5 | N/A |
| Fresh S100 Yolk Batch #3 | 129.12 | 3,800 | 490,656 | — | 82.30 | 0.64 |
| Yolk in .06 M Acetate | 11.68 | 56,500 | 660,146 | 100.00 | 71.90 | 6.15 |
| Yolk in .06 M Acetate 1% Cap. | 11.65 | 57,560 | 670,804 | 101.61 | 70.00 | 6.01 |
| Filtrate/Aqu. Layer Combined | 1.86 | 53,350 | 99,231 | 15.03 | 2.87 | 1.54 |
| Precipitate* | 73.93 | 34,862 | 57,720 | 39.04 | 10.00 | 0.14 |
| 100K Permeate #1 | 0.09 | 78,210 | 6,648 | 1.01 | 0.02 | 0.19 |
| 100K Permeate #2 | 0.15 | 74,770 | 10,991 | 1.66 | 0.02 | 0.15 |
| 100K Retentate #1 | 14.91 | 2,790 | 41,599 | 6.30 | 37.9 | N/A |
| 100K Retentate #2 | 13.78 | 3,230 | 44,509 | 6.74 | 36.3 | N/A |
| Fresh S100 Yolk Batch #4 | 125.18 | 3,460 | 433,123 | — | 125.60 | 1.00 |
| Yolk in .06 M Acetate | 11.57 | 51,900 | 600,327 | 100.00 | 159.30 | 13.77 |
| Yolk in .06 M Acetate 1% Cap. | 11.59 | 52,309 | 606,261 | 100.99 | 115.00 | 9.92 |
| Filtrate/Aqu. Layer Combined | 2.26 | 47,260 | 106,808 | 17.79 | 5.60 | 2.48 |
| Precipitate* | 80.30 | 3,457 | 277,597 | 46.24 | 16.40 | 0.20 |
| 100K Permeate #1 | 0.12 | 68,920 | 8,408 | 1.40 | 0.03 | 0.26 |
| 100K Permeate #2 | 0.13 | 76,140 | 9,822 | 1.64 | 0.04 | 0.28 |
| 100K Retentate #1 | 16.02 | 3,080 | 49,342 | 8.22 | 60.4 | N/A |
| 100K Retentate #2 | 13.47 | 3,860 | 51,990 | 8.66 | 22.80 | 1.69 |

*Protein and volume are in mg/ml and ml, respectively.

We claim:

1. A method for reducing the development of atheromatous lesions in a mammal being fed a high-cholesterol diet (HCD) to levels lower than those in said mammal being fed a HCD when untreated, said method comprising orally administering to said mammal egg or a fraction thereof, wherein said egg is produced by a method comprising:

immunizing a female avian with a composition comprising at least one bacterial antigen from each of the following bacterial strains: *Staphylococcus aureus, Staphylococcus epidermidis, Streptococcus pyogenes* A. Type 1, *Streptococcus pyogenes* A. Type 3, *Streptococcus pyogenes* A. Type 5, *Streptococcus pyogenes* A. Type 8, *Streptococcus pyogenes* A. Type 12, *Streptococcus pyogenes* A. Type 14, *Streptococcus pyogenes* A. Type 18, *Streptococcus pyogenes* A. Type 22, *Aerobacter aerogenes, Escherichia coli, Salmonella enteritidis, Pseudomonas aeruginosa, Klebsiella pneumoniae, Salmonella typhimurium, Haemophilus influenzae, Streptococcus mitis, Proteus vulgaris, Shigella dysenteriae, Diplococcus pneumoniae, Propionibacter acnes* (anaerobe), *Streptococcus sanguis, Streptococcus salivarius, Streprococcus mutans*, and *Streptococcus agalactiae;* maintaining said female avian in a hyperimmune state by administering to said female avian booster injections of said composition, and collecting said egg from said female avian in said hyperimmune state.

2. The method of claim 1 wherein said egg fraction comprises egg white.

3. The method of claim 1 wherein said egg fraction comprises egg yolk IgY fraction.

4. A method for lowering serum cholesterol in a mammal being fed a HCD to levels lower than those in said bring fed a HCD when untreated, said method comprising orally administering to said mammal egg or a fraction thereof, wherein said egg is produced by a method comprising:

immunizing a female avian with a composition comprising at least one bacterial antigen derived from each of the following bacterial strains: *Staphylococcus aureus, Staphylococcus epidermidis, Streptococcus pyogenes* A. Type 1, *Streptococcus pyogenes* A. Type 3, *Streptococcus pyogenes* A. Type 5, *Streptococcus pyogenes* A. Type 8, *Streptococcus pyogenes* A. Type 12, *Streptococcus pyogenes* A. Type 14, *Streptococcus pyogenes* A Type 18, *Streptococcus pyogenes* A. Type 22, *Aerobacter aerogenes, Escherichia coli, Salmonella enteritidis, Pseudomonas aeruginosa, Klebsiella*

*pneumoniae, Salmonella typhimurium, Haemophilus influenzae, Streptococcus mitis, Proteus vulgaris, Shigella dysenteriae, Diplococcus pneumoniae, Propionibacter acnes* (anaerobe), *Streptococcus sanguis, Streptococcus salivarius, Streptococcus mutans,* and *Streptococcus agalactiae,* maintaining said female avian in a hyperimmune state by administering to said female avian booster injections of said composition; and collecting said egg from said female avian in said hyperimmune state.

5. The method of claim 4 wherein said egg fraction comprises egg white.

6. The method of claim 4 wherein said egg fraction comprises egg yolk IgY fraction.

7. A method for lowering the level of lipid deposits in the aorta of a mammal, said method comprising administering to said mammal, egg or egg product in an amount and for a time sufficient to produce said lipid lowering effect, wherein said egg is produced by a method comprising:

immunizing a female avian with at least one antigen from *Aerobacter aerogenes;* maintaining said female avian in a hyperimmune state by administering to said female avian booster injections of said bacterial antigen; and collecting said egg from said female avian in said hyperimmune state.

8. A method for maintaining the level of lipid deposits in the aorta of a mammal comprising administering an egg or egg product to a mammal, wherein said egg or egg product does not alter the level of lipid deposits in the aorta of said mammal from those levels found in said mammal prior to administration, said method comprising administering to said mammal, egg or egg product in an amount and for a time sufficient to produce said lipid-maintaining effect, wherein said egg is produced by a method comprising:

immunizing a female avian with a composition comprising at least one antigen from each of the following bacterial strains: *Aerobacter aerogenes, Escherichia coli, Staphylococcus aureus, Staphylococcus epidermidis, Streptococcus pyogenes* A. Type 1, *Streptococcus pyogenes* A. Type 3, *Streptococcus pyogenes* A. Type 5, *Streptococcus pyogenes* A. Type 8, *Streptococcus pyogenes* A. Type 12, *Streptococcus pyogenes* A. Type 14, *Streptococcus pyogenes* A. Type 18, *Streptococcus pyogenes* A. Type 22, *Salmonella enteritidis, Pseudomonas aeruginosa, Klebsiella pneumoniae, Salmonella typhimurium, Haemophilus influenzae, Streptococcus mitis, Proteus vulgaris, Shigella dysenteriae, Diplococcus pneumoniae, Propionibacter acnes* (anaerobe), *Streptococcus sanguis, Streptococcus salivarius, Streptococcus mutans,* and *Streptococcus agalactiae;* maintaining said female avian in a hyperimmune state by administering to said female avian booster injections of said composition; and collecting said egg from said female avian in said hyperimmune state.

9. A method for maintaining the level of lipid deposits in the aorta of a mammal comprising administering an egg or egg product to a mammal wherein said egg or egg product does not alter the level of lipid deposits in the aorta of said mammal from the levels found in said mammal prior to administration, said method comprising administering to said mammal, egg or egg product in an amount and for a time sufficient to produce said lipid-maintaining effect, wherein said egg is produced by a method comprising:

immunizing a female avian with a composition comprising at least one antigen from each of the following bacterial strains: *Aerobacter aerogenes, Escherichia coli, Salmonella enteritidis, Pseudomonas aeruginosa, Klebsiella pneumoniae, Salmonella typhimurium, Haemophilus influenzae, Proteus vulgaris,* and *Shigella dysenteriae;* maintaining said female avian in a hyperimmune state by administering to said female avian booster injections of said composition; and collecting said egg from said female avian in said hyperimmune state.

10. A method for lowering the level of lipid deposits in the aorta of a mammal compared to the level of lipid deposits in the aorta of a mammal ingesting a normal egg comprising administering egg or egg product to a mammal wherein said egg or egg product does not elevate the level of lipid deposits in the aorta of said mammal to the level of lipid deposits found in the aorta of said mammal ingesting a normal egg, said method comprising administering to said mammal, egg or egg product in an amount and for a time sufficient to produce said lipid lowering effect, wherein said egg is produced by a method comprising:

immunizing a female avian with at least one antigen from at least one bacterial strain, said strain being selected from the group consisting of *Escherichia coli, Salmonella enteritidis, Pseudomonas aeruginosa, Klebsiella pneumoniae,* and *Shigella dysenteriae;* maintaining sad female avian in a hyperimmune state by administering to said female avian booster injections of said bacterial antigen; and collecting said eggs from said female avian in said hyperimmune state.

11. A method for maintaining the level of lipid deposits in the liver of a mammal comprising administering an egg or egg product to a mammal wherein said egg or egg product does not alter the level of lipid deposits in the liver of said mammal from those levels found in said mammal prior to administration, said method comprising administering to said mammal, egg or egg product in an amount and for a time sufficient to produce said lipid-maintaining effect, wherein said egg is produced by a method comprising:

immunizing a female avian with a composition comprising at least one bacterial antigen from each of the following bacterial strains: *Staphylococcus aureus, Staphylococcus epidermidis, Streptococcus pyogenes* A. Type 1, *Streptococcus pyogenes* A. Type 3, *Streptococcus pyogenes* A. Type 5, *Streptococcus pyogenes* A. Type 8, *Streptococcus pyogenes* A. Type 12, *Streptococcus pyogenes* A. Type 14, *Streptococcus pyogenes* A. Type 18, *Streptococcus pyogenes* A. Type 22, *Aerobacter aerogenes, Escherichia coli, Salmonella enteritidis, Pseudomonas aeruginosa, Klebsiella pneumoniae, Salmonella typhimurium, Haemophilus influenzae, Streptococcus mitis, Proteus vulgaris, Shigella dysenteriae, Diplococcus pneumoniae, Propionibacter acnes* (anaerobe), *Streptococcus sanguis, Streptococcus salivarius, Streptococcus mutans,* and *Streptococcus agalactiae;* maintaining said female avian in a hyperimmune state by administering to said female avian booster injections of said composition; and collecting said egg from said female avian in said hyperimmune state.

12. A method for maintaining the level of lipid deposits in the liver of a mammal comprising administering an egg or egg product to a mammal wherein said egg or egg product does not alter the level of lipid deposits in the liver of said mammal from those levels found in said mammal prior to administration, which comprises administering to said mammal, egg or egg product in an amount and for a time sufficient to produce said lipid-maintaining effect, wherein said egg is produced by a method comprising:

immunizing a female avian with a composition comprising at least one bacterial antigen from each of the following bacterial strains: *Aerobacter aerogenes, Escherichia coli, Salmonella enteritidis, Pseudomonas aeruginosa, Klebsiella pneumoniae, Salmonella typhimurium, Haemophilus influenzae, Proteus vulgaris, Shigella dysenteriae* maintaining said female avian in a hyperimmune state by administering to said female avian booster injections of said composition; and collecting said egg from said female avian in said hyperimmune state.

13. A method for maintaining the level of lipid deposits in the liver of a mammal comprising administering an egg or egg product to a mammal wherein said egg or egg product does not alter the level of lipid deposits in the liver of said mammal from those levels found in said mammal prior to administration, which comprises administering to said mammal, egg or egg product in an amount and for a time sufficient to produce said lipid-maintaining effect, wherein said egg is produced by a method comprising:

immunizing a female avian with at least one bacterial antigen from at least one bacterial strain, said bacterial strains selected from the group consisting of *Aerobacter aerogenes* and *Escherichia coli;* maintaining said female avian in a hyperimmune state by administering to said female avian booster injections of said bacterial antigen; and collecting said egg from said female avian in said hyperimmune state.

14. A method for lowering the level of lipid deposits in the liver of a mammal compared to the level of lipid deposits in the liver of a mammal ingesting a normal egg comprising administering egg or egg product to a mammal wherein said egg or egg product does not elevate the level of lipid deposits in the liver of said mammal to the level of lipid deposits found in the liver of said mammal ingesting a normal egg, said method comprising administering to said mammal, egg or egg product in an amount and for a time sufficient to produce said lipid-lowering effect, wherein said egg is produced by a method comprising:

immunizing a female avian with at least one antigen from at least one bacterial strain, said strain being selected from the group consisting of *Salmonella enteritidis, Pseudomonas aeruginosa,* and *Klebsiella pneumoniae;* maintaining said female avian in a hyperimmune state by administering to said female avian booster injections of said bacterial antigen; and collecting said egg from said female avian in said hyperimmune state.

15. A method for lowering the serum cholesterol in a mammal compared to the level of serum cholesterol in a mammal ingesting a normal egg comprising administering egg or egg product to a mammal wherein said egg or egg product does not elevate the level of serum cholesterol in said mammal to the level found in said mammal ingesting a normal egg, said method comprising administering to said mammal, egg or egg product in an amount and for a time sufficient to produce said serum cholesterol lowering effect, wherein said egg is produced by a method comprising:

immunizing a female avian with a composition comprising at least one antigen from each of the following bacterial strains: *Aerobacter aerogenes, Escherichia coli, Salmonella enteritidis, Pseudomonas aeruginosa, Klebsiella pneumoniae, Salmonella typhimurium, Haemophilus influenzae, Proteus vulgaris,* and *Shigella dysenteriae;* maintaining said female avian in a hyperimmune state by administering to said female avian booster injections of said composition; and collecting said egg from said female avian in said hyperimmune state.

16. A method for lowering the serum cholesterol in a mammal compared to the level of serum cholesterol in a mammal ingesting a normal egg comprising administering egg or egg product to a mammal wherein said egg or egg product does not elevate the level of serum cholesterol in said mammal to levels found in said mammal ingesting a normal egg, said method comprising administering to said mammal, egg or egg product in an amount and for a time sufficient to produce said serum cholesterol lowering effect, wherein said egg is produced by a method comprising:

immunizing a female avian with a composition comprising at least one antigen from each of the following bacterial strains: *Streptococcus pyogenes* A. Type 1, *Streptococcus pyogenes* A. Type 3, *Streptococcus pyogenes* A. Type 5, *Streptococcus pyogenes* A. Type 8, *Streptococcus pyogenes* A. Type 12, *Streptococcus pyogenes* A. Type 14, *Streptococcus pyogenes* A. Type 18, and *Streptococcus pyogenes* A. Type 22;

maintaining said female avian in a hyperimmune state by administering to said female avian booster injections of said composition; and collecting said egg from said female avian in said hyperimmune state.

17. A method for lowering the serum cholesterol in a mammal compared to the level of serum cholesterol in a mammal ingesting a normal egg comprising administering egg or egg product to a mammal wherein said egg or egg product does not elevate the level of serum cholesterol in said mammal to levels found in said mammal ingesting a normal egg, said method comprising administering to said mammal, egg or egg product in an amount and for a time sufficient to produce said serum cholesterol lowering effect, wherein said egg is produced by a method comprising:

immunizing a female avian with at least one bacterial antigen from at least one bacterial strain, said bacterial strains selected from the group consisting of *Aerobacter aerogenes, Escherichia coli, Salmonella enteritidis, Pseudomonas aeruginosa, Klebsiella pneumoniae, Salmonella typhimurium, Haemophilus influenzae,* and *Proteus vulgaris;* maintaining said female avian in a hyperimmune state by administering to said female avian booster injections of said bacterial antigen; and collecting said egg from said female avian in said hyperimmune state.

18. The method of any one of claims 1, 4 or 7–17 wherein said warm-blooded animal is a human.

* * * * *

UNITED STATES PATENT AND TRADEMARK OFFICE
CERTIFICATE OF CORRECTION

PATENT NO. : 5,853,765

DATED : December 29, 1998

INVENTOR(S) : Stolle et al.

It is certified that error appears in the above-identified patent and that said Letters Patent is hereby corrected as shown below:

Title page, [56] References Cited, U.S. PATENT DOCUMENTS, line 7, "4,536,384  8/1985" should read --4,636,384  1/1987--.

UNITED STATES PATENT AND TRADEMARK OFFICE
CERTIFICATE OF CORRECTION

PATENT NO. : 5,853,765
DATED : December 29, 1998
INVENTOR(S) : Stolle et al.

It is certified that error appears in the above-identified patent and that said Letters Patent is hereby corrected as shown below:

Columns 13-14, lines 10-39, Table 1 should read as follows:

Table 1

Bacterial Species Composition of
14 Different Vaccines (A-N) Used to Immunize Chickens

| Bacteria | Vaccine | | | | | | | | | | | | | |
|---|---|---|---|---|---|---|---|---|---|---|---|---|---|---|
| | A | B | C | D | E | F | G | H | I | J | K | L | M | N |
| Staph. aureus | + | + | | | | | | | | | | | | |
| Staph. epidermidis | + | + | | | | | | | | | | | | |
| Strep. pyogenes, A. Type 1 | + | + | | | | | | | | | | | | |
| Strep. pyogenes, A. 3 | + | + | | | | | | | | | | | | |
| Strep. pyogenes, A. 5 | + | + | | | | | | | | | | | | |
| Strep. pyogenes, A. 8 | + | + | | | | | | | | | | | | |
| Strep. pyogenes, A. 12 | + | + | | | | | | | | | | | | |
| Strep. pyogenes, A. 14 | + | + | | | | | | | | | | | | |
| Strep. pyogenes, A. 18 | + | + | | | | | | | | | | | | |
| Strep. Pyogenes, A. 22 | + | + | | | | | | | | | | | | |
| Aerobacter aerogenes | + | | | | + | + | | | | | | | | |
| Escherichia coli | + | | | | + | | + | | | | | | | |
| Salmonella enteritidis | + | | | | + | | | + | | | | | | |
| Pseudomonas aeruginosa | + | | | | + | | | | + | | | | | |
| Klebsiella pneumoniae | + | | | | + | | | | | + | | | | |
| Salmonella typhimurium | + | | | | + | | | | | | + | | | |
| Haemophilus influenzae | + | | | | + | | | | | | | + | | |
| Strep. mitis | + | | + | | | | | | | | | | | |
| Proteus vulgaris | + | | | | + | | | | | | | | + | |
| Shigella dysenteriae | + | | | | + | | | | | | | | | + |
| Diplococcus pneumoniae | + | | + | | | | | | | | | | | |
| Propionibacter acnes (anaerobe) | + | | + | | | | | | | | | | | |
| Strep. sanguis | + | | + | | | | | | | | | | | |
| Strep. salivarius | + | | + | | | | | | | | | | | |
| Strep. mutans | + | | + | | | | | | | | | | | |
| Strep. agalactiae | + | | + | | | | | | | | | | | |

UNITED STATES PATENT AND TRADEMARK OFFICE
CERTIFICATE OF CORRECTION

PATENT NO.  : 5,853,765
DATED       : December 29, 1998
INVENTOR(S) : Stolle et al.

It is certified that error appears in the above-identified patent and that said Letters Patent is hereby corrected as shown below:

Columns 25-26, in Table 6, 4th Column, line 11 under the sub-heading "T Prot. (mg)", "27,886" should read --27,866--.

Column 26, line 53, "bring" should read --mammal being--.

Column 28, line 30, "sad" should read --said--.

Column 29, line 14, after "dysenteriae" insert a comma (,).

Column 30, line 63, in claim 18, "7-17" should read --7-15--.

Signed and Sealed this

Second Day of January, 2001

Attest:

*Attesting Officer*

Q. TODD DICKINSON

*Commissioner of Patents and Trademarks*